US012758435B2

(12) United States Patent
DeGrave et al.

(10) Patent No.: US 12,758,435 B2
(45) Date of Patent: Oct. 13, 2026

(54) APPARATUSES AND METHODS FOR MANUFACTURING ABSORBENT STRUCTURES INCLUDING FLEXIBLE MASKING MEDIA

(71) Applicant: Kimberly-Clark Worldwide, Inc., Neenah, WI (US)

(72) Inventors: Greg J. DeGrave, Combined Locks, WI (US); Andrew E. Neubauer, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 515 days.

(21) Appl. No.: 17/612,470

(22) PCT Filed: May 30, 2019

(86) PCT No.: PCT/US2019/034560
§ 371 (c)(1),
(2) Date: Nov. 18, 2021

(87) PCT Pub. No.: WO2020/242475
PCT Pub. Date: Dec. 3, 2020

(65) Prior Publication Data
US 2022/0257428 A1 Aug. 18, 2022

(51) Int. Cl.
*A61F 13/15* (2006.01)
*B05B 12/24* (2018.01)
*D04H 1/724* (2012.01)

(52) U.S. Cl.
CPC ........ *A61F 13/15658* (2013.01); *B05B 12/24* (2018.02); *D04H 1/724* (2013.01); *A61F 2013/15926* (2013.01)

(58) Field of Classification Search
CPC ..... A61F 13/15658; A61F 2013/15926; D04H 1/724
See application file for complete search history.

(56) References Cited

U.S. PATENT DOCUMENTS 3,846,871 A 11/1974 Kolbach
4,388,056 A 6/1983 Lee et al.
(Continued)

FOREIGN PATENT DOCUMENTS

CN 102505347 A 6/2012
EP 0388020 A1 9/1990
(Continued)

OTHER PUBLICATIONS

Wubbe, Eileen, "Air Through Bulks Up", Jun. 2005, Nonwoven Industry, https://www.nonwovens-industry.com/contents/view_features/2005-06-14/air-through-bulks-up/15302.

*Primary Examiner* — George R Koch
(74) *Attorney, Agent, or Firm* — KIMBERLY-CLARK WORLDWIDE, INC.

(57) ABSTRACT

Methods and apparatuses for forming fibrous web structures are disclosed. In one embodiment, a method of forming a fibrous web comprises positioning a masking media over a foraminous forming member having a forming surface, the masking media producing covered portions and uncovered portions of the forming surface, applying vacuum pressure so as to draw air through the forming surface, depositing fibrous material onto the forming surface to form a fibrous web. The masking media may be flexible such that the at least one masking media is sucked tight to the forming surface and forms direct contact with the forming surface where vacuum pressure is applied, thereby preventing the fibrous material from flowing between the at least one masking media and the forming surface.

20 Claims, 12 Drawing Sheets

(56) References Cited

U.S. PATENT DOCUMENTS

| | | | | |
|---|---|---|---|---|
| 4,666,647 | A | 5/1987 | Enloe et al. | |
| 4,995,141 | A | 2/1991 | Gould | |
| 5,004,579 | A * | 4/1991 | Wislinski | A61F 13/15577 425/81.1 |
| 5,076,774 | A | 12/1991 | Farrington et al. | |
| 6,981,297 | B2 | 1/2006 | Venturino et al. | |
| 7,232,300 | B2 | 6/2007 | Walter et al. | |
| 9,464,371 | B2 | 10/2016 | Matsunaga et al. | |
| 2012/0018078 | A1 | 1/2012 | Ishikawa | |
| 2012/0270715 | A1 | 10/2012 | Motegi et al. | |
| 2014/0305570 | A1 * | 10/2014 | Matsunaga | D04H 1/732 156/62.2 |

FOREIGN PATENT DOCUMENTS

| | | | |
|---|---|---|---|
| JP | 2009000386 | A | 1/2009 |
| JP | 2012135470 | A | 7/2012 |
| JP | 2017196048 | A * | 11/2017 |

* cited by examiner

APPARATUSES AND METHODS FOR MANUFACTURING ABSORBENT STRUCTURES INCLUDING FLEXIBLE MASKING MEDIA

TECHNICAL FIELD

The field of this disclosure relates generally to absorbent structures and methods of manufacturing absorbent structures for use in absorbent articles, such as training pants, diapers, incontinence products, disposable underwear, medical garments, feminine care articles, absorbent swim wear, and the like.

BACKGROUND OF THE DISCLOSURE

In one general practice of forming fibrous webs, such as laid fibrous webs, a fibrous sheet of cellulosic or other suitable absorbent material is fiberized in a conventional fiberizer, or other suitable shredding or comminuting device, to form discrete fibers. In some practices, particles of superabsorbent material may be mixed with the fibers. The fibers, and optionally superabsorbent particles, are then entrained in an air stream and directed to a suitable foraminous forming surface upon which the fibers and superabsorbent particles are deposited to form a continuous absorbent fibrous web or discrete absorbent fibrous web structures.

The forming surfaces utilized in such systems are typically constructed with a wire or screen grid and employ a suitable pneumatic flow mechanism, such as a vacuum suction apparatus, to define a differential pressure zone on the forming surface and impose a pressure differential thereon. The pressure difference usually results in airflow through the openings or perforations in the screen or grid of the forming surface, thereby drawing the air-entrained fiber, and optionally superabsorbent particles, stream onto the forming surface. This type of forming operation has been employed in high-speed commercial operations.

According to some processes, the forming surface may be a continuous surface such that the air-entrained fibers, and optionally superabsorbent particles, are drawn onto the forming surface to form a continuously extending fibrous web structure. This continuously extending web structure may further be processed into individual, discrete segments for use in articles such as training pants, diapers, incontinence products, disposable underwear, medical garments, feminine care articles, absorbent swim wear, and other similar absorbent article products. In other processes, the forming surface may have discrete foraminous portions separated by non-foraminous portions. In such processes, the air-entrained fibers, and optionally superabsorbent particles, are drawn to the discrete foraminous portions of the forming surface, thereby forming individual, discrete absorbent fibrous web structures.

In order to form the air-entrained fiber, and optionally superabsorbent particle, stream into a desired shape, one or more masking media are positioned over the foraminous forming surface. These one or more masking media cover some portions of the foraminous forming surface and leave other portions of the foraminous forming surface uncovered. The air-entrained fiber and particle stream deposits onto the uncovered portions of the foraminous forming surface, thereby forming a desired shape of the continuous web or discrete absorbent structures. In some cases, the masking media may be employed not only to define a shape of the continuous web or discrete absorbent structures, but may also help to provide basis-weight zoning of the continuous web or discrete absorbent structures. Such masking media are typically rigid metal masking plates formed as segments with each segment having a curvature matching a curvature of the forming surface.

When forming a continuous fibrous absorbent web or discrete absorbent fibrous web structures in a high speed commercial operation, ensuring consistent and clean release of the continuous web or the discrete absorbent structures from the forming surface and the masking media can represent a challenge. Accordingly, it is desirable to provide more reliable and more efficient methods and apparatus for forming laid fibrous webs, whether continuous or discrete, and/or forming zoned areas of basis weight. It is further desirable to provide methods and apparatuses for use in high speed manufacturing operations which can consistently and cleanly form and separate a continuous fibrous absorbent web or discrete absorbent fibrous web structures from a forming surface and masking media of a forming apparatus.

SUMMARY OF THE DISCLOSURE

The field of this disclosure relates generally to absorbent structures and methods of manufacturing absorbent structures for use in absorbent articles, such as training pants, diapers, incontinence products, disposable underwear, medical garments, feminine care articles, absorbent swim wear, and the like.

In a first embodiment a method of manufacturing a fibrous web may comprise moving a foraminous forming member in a machine direction, the foraminous forming member having a forming surface and at least one masking media disposed on the forming surface and covering portions of the forming surface and leaving portions of the forming surface uncovered, applying vacuum pressure along a portion of the foraminous member so as to draw air through the forming surface in a first direction, the at least one masking media substantially blocking the air from moving through the covered portions of the forming surface, depositing fibrous material onto the forming surface to form an fibrous web corresponding to the uncovered portions of the forming surface, and disengaging the formed fibrous web from the forming surface. The at least one masking media may be flexible such that the at least one masking media is sucked tight to the forming surface and forms direct contact with the forming surface along the portion of the forming surface where vacuum pressure is applied, thereby preventing the fibrous material from flowing between the at least one masking media and the forming surface.

In another embodiment, an apparatus for forming fibrous web structures may comprise a foraminous forming member having a forming surface and comprising a vacuum zone and a blow-off zone, wherein air is drawn through the forming surface in a first direction in the vacuum zone, at least one masking media disposed on the forming surface, the at least one masking media covering portions of the forming surface and leaving portions of the forming surface uncovered, and a fiber deposition apparatus disposed about the foraminous member and configured to introduce fibrous material proximate the foraminous member vacuum zone. The at least one masking media may be flexible such that the at least one masking media is sucked tight to the forming surface and forms direct contact with the forming surface along the portion of the foraminous member vacuum zone, thereby preventing the introduced fibrous material from flowing between the at least one masking media and the forming surface.

BRIEF DESCRIPTION OF DRAWINGS

The present disclosure will be more fully understood, and further features will become apparent, when reference is made to the following detailed description and the accompanying drawings. The drawings are merely representative and are not intended to limit the scope of the claims.

Figure 1:
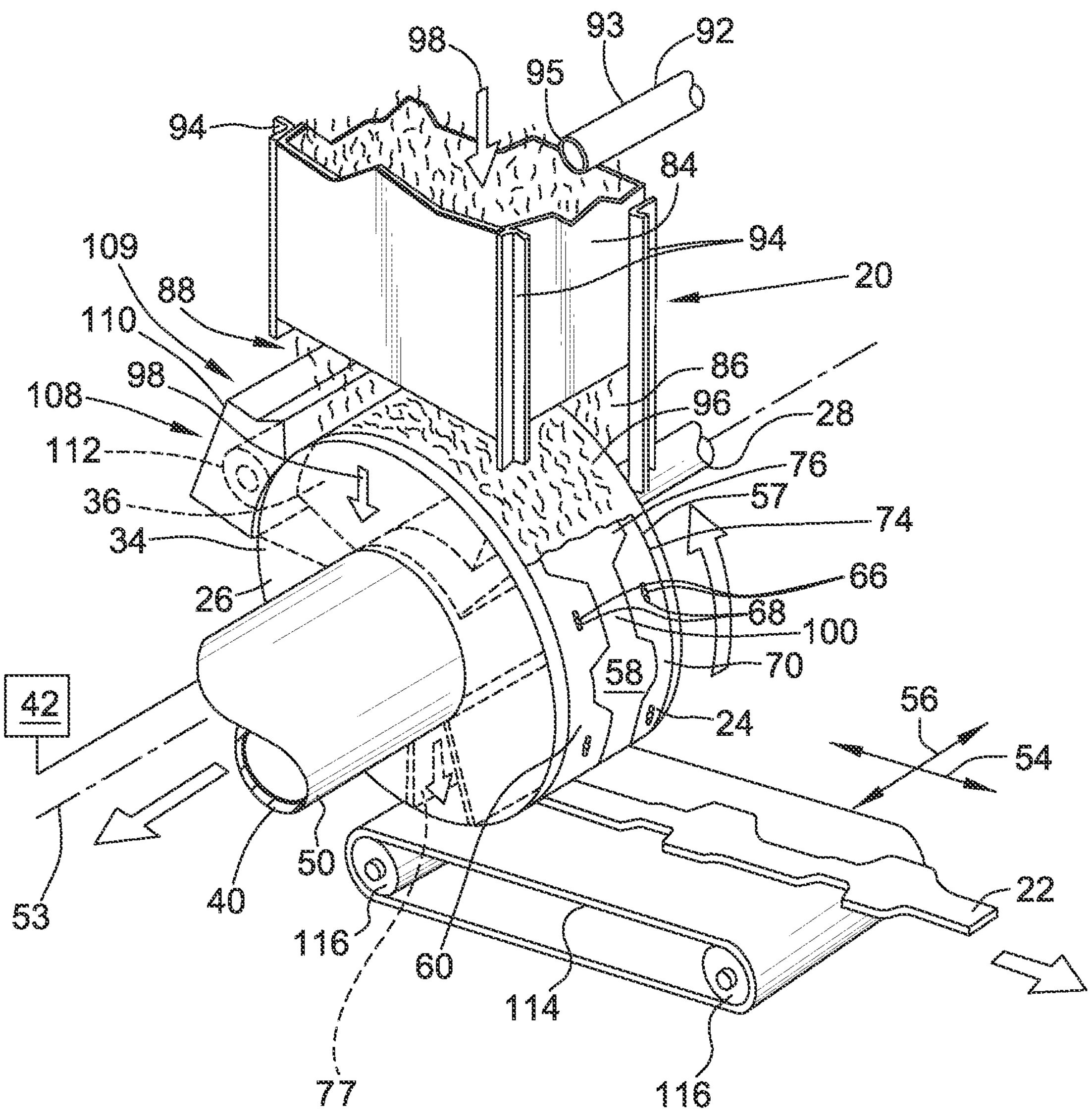
FIG. 1 is a perspective view of one suitable embodiment of a forming assembly for forming fibrous webs.

Repeat use of reference characters in the present specification and drawings is intended to represent the same or analogous features or elements of the disclosure. Additionally, while the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION OF THE DISCLOSURE

It is to be understood by one of ordinary skill in the art that the present discussion is a description of exemplary aspects of the present disclosure only, and is not intended as limiting the broader aspects of the present disclosure.

Figure 2:
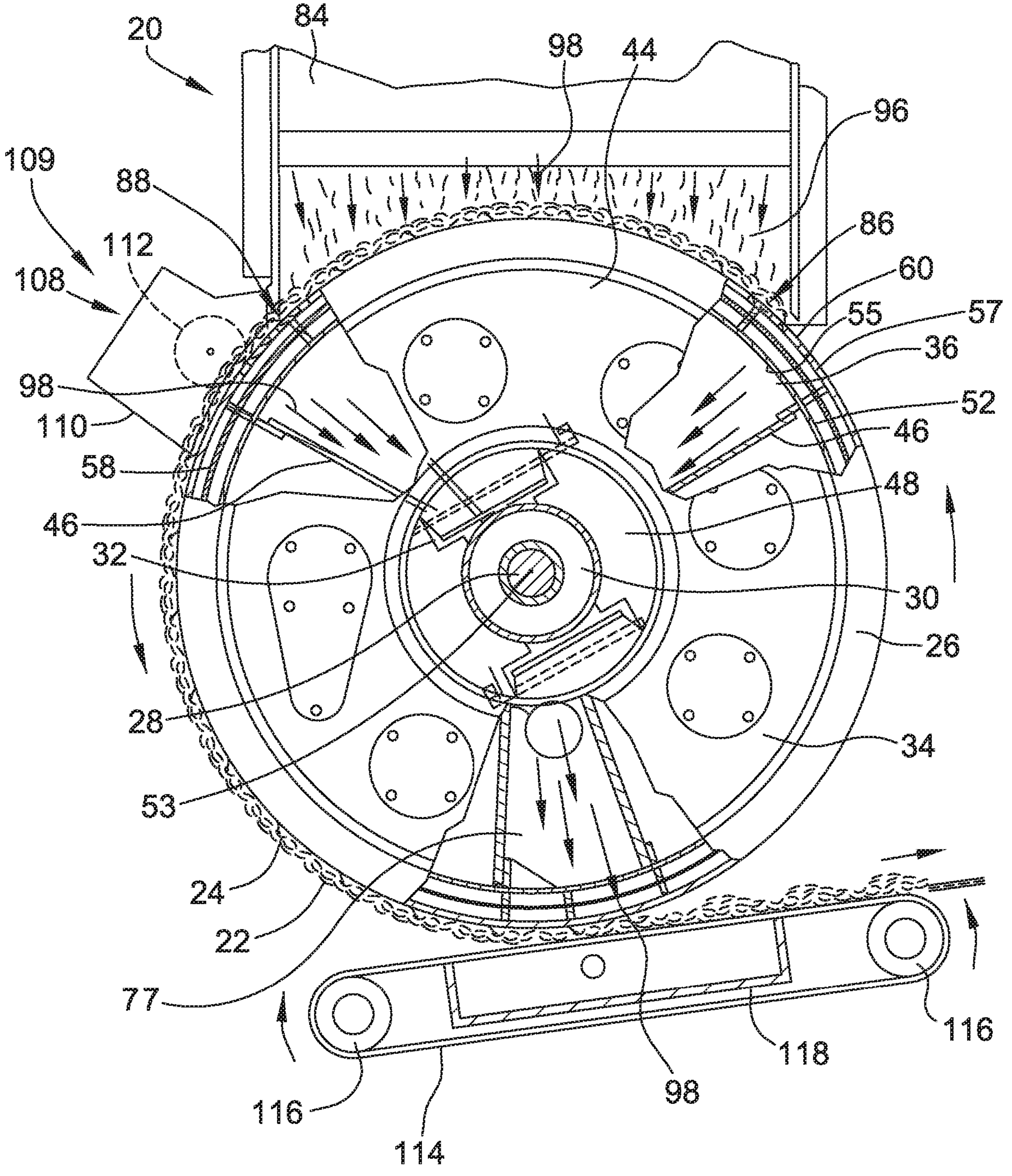
FIG. 2 is a side view of the forming assembly of FIG. 1 with portions removed to reveal inner parts.

With reference now to the drawings, and in particular to FIGS. 1 and 2, an apparatus for forming an absorbent fibrous web structure is illustrated and indicated generally by reference number 20. Apparatus 20 includes a movable, foraminous forming surface 24 extending around the circumference of a forming drum 26. The forming drum 26 is mounted on a shaft 28 connected by bearings 30 to a support 32. The forming drum 26 includes a circular drum wall (not shown) operatively connected to and rotated by the drum drive shaft 28. The shaft 28 is driven in rotation by a suitable motor or line shaft (not shown) in a counterclockwise direction as seen in FIG. 2. The drum wall can be a primary, load-bearing member, and the drum wall can extend generally radially and circumferentially about the drum drive shaft 28.

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Connected" refers to the joining, adhering, bonding, attaching, or the like, of two elements. Two elements will be considered to be connected together when they are connected directly to one another or indirectly to one another, such as when each is directly connected to intermediate elements.

"Cross direction" refers to the width of a fabric in a direction generally perpendicular to the direction in which it is produced, as opposed to "machine direction" that refers to the length of a fabric in the direction in which it is produced.

"Cross direction assembly" refers to a process in which disposable absorbent products are manufactured in an orientation in which the products are connected side-to-side, a process utilizing a cross direction assembly that entails products traveling through a converting machine parallel to the direction of arrow 54, as opposed to "machine direction assembly" in which the products are connected end-to-end or waist-to-waist.

"Disposable" refers to articles that are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite that can be elongated by at least 25 percent of its relaxed length and that will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to any woven, knitted and nonwoven fibrous webs.

"Film" refers to a thermoplastic film made using a film extrusion and/or forming process, such as a cast film or blown film extrusion process. The term includes apertured films, slit films, and other porous films that constitute liquid transfer films, as well as films that do not transfer liquid.

"Flexible" refers to materials that are compliant and that will readily conform to the general shape and contours of the wearer's body.

"Hydrophilic" describes fibers or the surfaces of fibers that are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 are designated "wettable" or hydrophilic, while fibers having contact angles greater than 90 are designated "nonwettable" or hydrophobic.

"Integral" or "integrally" is used to refer to various portions of a single unitary element rather than separate structures bonded to or placed with or placed near one another.

"Layer" when used in the singular can have the dual meaning of a single element or a plurality of elements.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, can spread or be transported parallel to the plane of the liquid impermeable layer or laminate, but this is not considered to be within the meaning of "liquid impermeable" when used herein.

"Liquid permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

"Longitudinal" and "transverse" have their customary meaning, as indicated by the longitudinal and transverse axes depicted in FIGS. 1 and 2. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Machine direction" refers to the length of a fabric in the direction in which it is produced, as opposed to "cross direction" that refers to the width of a fabric in a direction generally perpendicular to the machine direction.

"Machine direction assembly" refers to a process in which disposable absorbent products are manufactured in an orientation in which the products are connected end-to-end or waist-to-waist, a process utilizing a machine direction assembly entails products traveling through a converting machine, as opposed to "cross direction assembly" in which the products are connected side-to-side.

"Meltblown fiber" means fibers formed by extruding a molten thermoplastic material through a plurality of fine, usually circular, die capillaries as molten threads or filaments into converging high velocity heated gas (e.g., air) streams that attenuate the filaments of molten thermoplastic material to reduce their diameter, which can be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers that can be continuous or discontinuous, are generally smaller than about 0.6 denier, and are generally self-bonding when deposited onto a collecting surface. Meltblown fibers used in the present disclosure are preferably substantially continuous in length.

"Member" when used in the singular can have the dual meaning of a single element or a plurality of elements.

"Nonwoven" and "nonwoven web" refer to materials and webs of material that are formed without the aid of a textile weaving or knitting process.

"Operatively joined," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Permanently bonded" refers to the joining, adhering, connecting, attaching, or the like, of two elements of an absorbent garment such that the elements tend to be and remain bonded during normal use conditions of the absorbent garment.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Refastenable" refers to the property of two elements being capable of releasable attachment, separation, and subsequent releasable reattachment without substantial permanent deformation or rupture.

"Releasably attached," "releasably engaged," and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment. It should be noted that a releasably attached or releasably engaged seam is a refastenable seam that does not include a bonded seam that must be torn, cut, or otherwise disrupted.

"Spunbonded fiber" refers to small diameter fibers that are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, to at least 150% of its initial (unstretched) length in at least one direction, suitably to at least 200% of its initial length, desirably to at least 250% of its initial length.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and that substantially returns to a nonsoftened condition when cooled to room temperature.

These terms can be defined with additional language in the remaining portions of the specification.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

A vacuum duct 36 located radially inwardly of the forming surface 24 extends over an arc of the interior of the forming drum 26. The vacuum duct 36 is in fluid communication with the forming surface 24 for drawing air through the forming surface 24. The vacuum duct 36 is mounted on and in fluid communication with a vacuum supply conduit 40 connected to a vacuum source 42. The vacuum source 42 may be any conventional vacuum generating mechanism such as, for example, a vacuum pump, an exhaust blower or fan or other suitable mechanism which can provide a relatively lower pressure under the forming surface 24. The vacuum duct 36 is connected to the vacuum supply conduit 40 along an outer peripheral surface of the vacuum supply conduit 40, and extends circumferentially around the vacuum supply conduit 40. The vacuum duct 36 projects radially outwardly from the vacuum supply conduit 40 toward the forming surface 24 and includes axially spaced side walls 44 and angularly spaced end walls 46. In some embodiments, the vacuum duct 36 may extend over a relatively large arc of the drum 26. For example, the vacuum duct 36 may extend the exit 88 of the forming chamber 84 all the way to the blow-off zone 77 such that an end wall 46 of the vacuum duct 36 comprises the end wall of both the vacuum duct 36 and the blow-off zone 77. In other embodiments, however, the end wall 46 need not correspond to the both the vacuum duct 36 and the blow-off zone 77. For instance, the vacuum duct 36 may extend beyond the scarfing zone 109 in the direction of rotation of the drum 26, but terminate prior to the blow-off zone 77 such that the end wall 46 does not correspond to an end wall of the blow-off zone 77.

The shaft 28 extends through the drum wall and into the vacuum supply conduit 40 where it is received in the bearing 30 connected to the support 32 within the vacuum supply conduit 40. The bearing 30 is sealed with the vacuum supply conduit 40 so that air is not drawn in around the shaft 28 where it enters the vacuum supply conduit 40.

As representatively shown, the vacuum supply conduit 40 can include a conduit end wall 48 and a peripheral wall 50 that delimit the size and shape of the vacuum supply conduit 40. The vacuum supply conduit 40 can have any suitable cross-sectional shape. In the illustrated configuration, the vacuum supply conduit 40 has a generally circular cross-sectional shape. The vacuum supply conduit 40 can be operatively held in position with any suitable support structure. The support structure can also be joined and connected to further components or members that operatively support the portions of the vacuum supply conduit 40 structure that engage the drum drive shaft 28, such as the support 32. For example, in the exemplary embodiment, the support 32 and the entire vacuum supply conduit 40 are supported by an overhead mount (not shown).

In the illustrated embodiment, walls 34 extend generally radially and circumferentially about the vacuum supply conduit 40. A drum rim 52 is joined to the walls 34, and is constructed and arranged to provide a substantially free movement of air through the thickness of the drum rim 52. The drum rim 52 is generally cylindrical in shape and extends along the direction of the drum axis 53, and circumferentially about the drum axis 53. As representatively shown, the drum rim 52 can be supported by and extend between the walls 34. The drum rim 52 has an inward-facing surface 55 that faces the vacuum duct 36.

With reference to FIGS. 1 and 2, the forming surface 24 can be provided along the outer, cylindrical surface of the forming drum 26, and can extend along the axial and circumferential dimensions of the forming drum 26. The circumferential dimension is generally in a machine direction 54 and the axial dimension is generally in a cross-machine direction 56. The structure of the forming surface 24 can be composed of an assembly, and can include a foraminous member 58, which is operatively connected and joined to the forming drum 26. In the illustrated embodiment, a system of inserts 57 forms the forming surface 24 and the foraminous member 58.

The forming surface 24 can be operatively held and mounted on the drum rim 52 by employing any suitable attachment mechanism. As representatively shown, a system of nuts and bolts can be employed to secure the inserts 57 onto an operative set of mounting rings, and the mounting rings can be operatively mounted on and secured to the drum rim 52.

Suitable forming drum systems for producing airlaid fibrous webs, such as absorbent fibrous web structure 22, are well known in the art. For example, see U.S. Pat. No. 4,666,647 entitled APPARATUS AND METHOD FOR FORMING A LAID FIBROUS WEB by K. Enloe et al. which issued May 19, 1987; and U.S. Pat. No. 4,761,258 entitled CONTROLLED FORMATION OF LIGHT AND HEAVY FLUFF ZONES by K. Enloe which issued Aug. 2, 1988; the entire disclosures of which are incorporated herein by reference in a manner that is consistent herewith. Other forming drum systems are described in U.S. Pat. No. 6,330,735, entitled APPARATUS AND PROCESS FOR FORMING A LAID FIBROUS WEB WITH ENHANCED BASIS WEIGHT CAPABILITY by J. T. Hahn et al. which issued Dec. 18, 2001, the entire disclosure of which is incorporated herein by reference in a manner that is consistent herewith. Systems for forming surfaces are described in U.S. Pat. No. 6,630,088, entitled FORMING MEDIA WITH ENHANCED AIR FLOW PROPERTIES by Michael Barth Venturino et al. which issued Oct. 7, 2003, the entire disclosure of which is incorporated herein by reference in a manner that is consistent herewith.

In other embodiments, the apparatus 20 may have any type of forming surface 24. For example, the forming surface 24 may be provided by an endless forming belt. Forming belt systems for producing absorbent fibrous webs are well known in the art. Examples of such forming belt systems are available from the Paper Converting Machine Company, a business having offices located in Green Bay, Wis., U.S.A.; and from Curt G. Joa Incorporated, a business having offices located in Sheboygan Falls, Wis., U.S.A.

The apparatus 20 further includes a forming chamber 84 through which the forming surface 24 is movable. The forming chamber 84 has an entrance 86 where the forming surface 24 enters the chamber substantially free of fibrous material and an exit 88 where the forming surface 24 leaves the chamber substantially filled with fibrous material. A fiberizer (not shown) provides fibrous material into the forming chamber 84, and the vacuum source 42 creates a vacuum pressure in the vacuum duct 36 relative to the interior of the forming chamber 84. As the forming surface 24 enters and then traverses through the forming chamber 84, the component materials of the absorbent web 22 are operatively carried or transported by an entraining air stream that is drawn through the forming surface 24. The pressure differential across the forming surface 24 causes the fluent fibers in the forming chamber 84 to be drawn to the forming surface 24. The fibers, and other desired component materials of the absorbent web 22, may be entrained in any suitable gaseous medium. Accordingly, any references herein to air as being the entraining medium should be understood to be a general reference which encompasses any other operative entrainment gas.

The selected component materials of the absorbent web 22 may comprise fibrous material and/or superabsorbent material. The fibrous material may be suitably derived from a batt of cellulosic fibers (e.g., wood pulp fibers) or other source of natural and/or synthetic fibers, which has been disintegrated, in a manner well known in the art, to provide an operative quantity of individual, loose fibers. Accordingly, the fiberizer (not shown) can operatively receive a selected web-forming material, convert the web-forming material into individual fibers, and deliver the fibers into the forming chamber 84. The fiberizer can be a rotary hammer mill, a rotatable picker roll, or any other suitable fiberizer. In some embodiments, the fibers can be chemically altered or curled fibers.

Superabsorbent material, such as superabsorbent particles or fibers, may be introduced into the forming chamber 84 by employing conventional mechanisms, such as pipes, channels, spreaders, nozzles and the like, as well as combinations thereof. In the representatively shown configuration, the superabsorbent material can be delivered into the forming chamber 84 by employing a delivery system 92, such as the illustrated operative conduit and nozzle system. The illustrated operative conduit and nozzle system includes a conduit 93 and a nozzle 95. The illustrated orientation of the delivery conduit 93 is exemplary, and it should be readily appreciated that any operative orientation of the delivery conduit 93 and nozzle 95 may be employed. Exemplary options for introducing superabsorbent material into the forming chamber 84 include pneumatic transport and gravity feeding mechanisms. Superabsorbent materials are well known in the art, and are readily available from various suppliers. For example, FAVOR 880 superabsorbent is available from Stockhausen, Inc., a business having offices located in Greensboro, N.C., U.S.A.; and BASF 9700 is available from BASF Corporation, a business having offices located in Charlotte, N.C., U.S.A.

The particles or fibers of superabsorbent material may be introduced into the forming chamber 84 and deposited on the forming surface 24 such that the absorbent web 22 is formed with a desired percentage of superabsorbent material. Preferably, the absorbent web 22 may include between about 0% and 90% superabsorbent material. Even more preferably, the absorbent web 22 may include between about 50% and 80% superabsorbent material.

In suitable embodiments, the absorbent web 22 may have different amounts of superabsorbent material in different locations. For example, higher basis weight areas of the absorbent web 22 may have higher concentrations of superabsorbent material and lower basis weight areas may have lower concentrations of superabsorbent material. In other suitable embodiments, the superabsorbent material may be distributed uniformly throughout the absorbent web 22.

The stream of air-entrained fibers, and optionally superabsorbent particles, can pass through the forming chamber 84 for deposition onto the selected forming surface 24. The forming chamber 84 can serve to direct and concentrate the air-entrained fibers and particles, and to provide a desired velocity profile in the air-entrained stream of fibers and particles. Typically, the forming chamber 84 is supported by suitable structural members 94, which together form a support frame for the forming chamber 84. The frame may be anchored and/or joined to other suitable structural components, as necessary or desirable.

The portion of the forming drum 26 which, at a particular point in time, is positioned within the boundaries of the forming chamber 84 can delimit or otherwise provide a vacuum lay-down zone 96 of the forming surface 24. As representatively shown, the vacuum lay-down zone 96 can constitute a circumferential, cylindrical surface portion of the rotatable drum 26. An operative pressure differential is imposed on the surface of the vacuum lay-down zone 96 under the action of the vacuum source 42. The vacuum source 42 can operatively withdraw air from the arcuate segment of the forming drum 26 associated with the vacuum lay-down surface 96 through the vacuum duct 36 and the vacuum supply conduit 40. Accordingly, air flows through the forming chamber 84 and the forming drum 26 in the direction of arrows 98.

In a representative operation, the absorbent web 22 can be formed from the stream of air-entrained fibers (and optionally superabsorbent particles) as the entrainment gas flows through the openings in the forming surface 24 and into the rotating forming drum 26. Under the influence of the vacuum source 42, a conveying air stream is drawn through the forming surface 24 into the interior of the forming drum 26, and is subsequently passed out of the forming drum 26 through the vacuum supply conduit 40. As the air-entrained fibers (and optionally superabsorbent particles) impinge on the forming surface 24, the air component is passed through the forming surface 24 and the fibers-particles component is retained on the forming surface 24 to form the absorbent web 22 thereon. In suitable embodiments, a substrate can be positioned on the forming surface 24 to receive the deposited fibers (and optionally particles). The substrate is at least partly air-permeable so the entrainment gas can flow through the substrate and through the forming surface 24. In some of these embodiments, the substrate can be a nonwoven material. Accordingly, where a substrate is used, the fibers (and optionally superabsorbent particles) impinge on the substrate which is disposed on the forming surface 24 as opposed to directly onto the forming surface 24.

According to some aspects of the present disclosure, a masking media can be disposed on the foraminous member 58. An exemplary masking media according to the present disclosure may be masking media 60. The exemplary masking media 60 has side walls 70 which operate to displace the fibrous material (FIG. 1). The side walls 70 have outboard side edges 74 and inboard side edges 76. In desired arrangements, the inboard side edges 76 of the masking media 60 can be contoured. In the representatively shown arrangement, the side walls 70 of the masking media 60 has an undulating contour defined by the inboard side edges 76 along the machine direction 54. As shown in FIG. 1, the contoured nature of the masking media 60 provides alternating, narrow and wide regions over the forming surface 24 that allow air flow through the forming surface 24. In some embodiments, the masking media 60 can be symmetric such that the contours of the inboard side edges 76 can be substantially mirror images of each other. The inboard side edges 76 of the masking plates 60 can optionally have a substantially straight configuration along the machine-direction 54 to expose a substantially rectangular, ribbon shaped region of the foraminous member 58.

In many embodiments, the masking media 60, when overlaid on the forming surface 24, covers portions of the forming surface 24 and leaves portions of the forming surface uncovered so as to produce at least one open area 100. The side walls 70 of the masking media 60 substantially block air-flow through the portions of the forming surface 24 which are covered by the masking media 60. The uncovered, open area 100 is generally substantially free of obstructions to the deposition of web material on the forming surface 24. The blocking of the airflow through the portions of the forming surface 24 covered by the masking media 60 inhibits the deposition of fibrous material (and superabsorbent material in some embodiments) on such covered portions of the forming surface 24. Accordingly, the fibrous material (and superabsorbent material in some embodiments) preferentially deposits onto the open area 100 which is uncovered by the masking media 60. Preferably, the open area 100 has a continuous area between about 10 cm2 and about 750 cm2. More preferably, the open area 100 has a continuous area between about 200 cm2 and about 500 cm2.

After formation of the airlaid absorbent web 22, the drum 26 rotation can then pass the absorbent web 22 from the vacuum lay-down zone 96 to a scarfing zone 109 where excess thickness of the absorbent web 22 can be trimmed and removed to a predetermined extent by a scarfing system 108. The scarfing system 108 may be positioned at the exit region 88 of the forming chamber 84. Although, in other embodiments, the scarfing system 108 may be positioned further away from the forming chamber 84 in the direction of rotation of the drum 26—for example, proximate the blow-off zone 77.

The scarfing system 108 can include a scarfing chamber 110 and a scarfing roll 112, which is positioned within the scarfing chamber 110. The scarfing roll 112 can abrade excess fibrous material from the absorbent web 22, and the removed fibers can be transported away from the scarfing chamber 110 with a suitable discharge conduit, as is well known in the art. The removed fibrous material may, for example, be recycled back into the forming chamber 84 or the fiberizer, as desired. Optionally, the scarfing roll 112 can rearrange and redistribute the web material along the longitudinal machine direction 54 of the web and/or along the lateral cross-machine direction 56 of the absorbent web 22.

Substantial redistribution during the scarfing process to create areas of higher basis weight in the absorbent web 22 does not generally occur because the masking media 60 displaces the fibrous material forming the absorbent web 22 according to the desire shape and material distribution. However, in some suitable embodiments, the scarfing system 108 may be used to redistribute a relatively small amount of the fibrous material to further delineate the gradation in basis weight.

The rotatable scarfing roll 112 is operatively connected and joined to a suitable shaft member, and is driven by a suitable drive system (not shown). The drive system may include any conventional apparatus, such as a motor or a coupling to the drive mechanism employed to rotate the forming drum 26. The scarfing system 108 can provide a conventional trimming mechanism for removing or redistributing any excess thickness of the laid absorbent web 22 that has been deposited on the forming surface 24. The surface of the scarfing roll 112 can be adjusted to provide a desired contour along the scarfed surface of the absorbent web 22. In the representatively shown arrangement, the scarfing roll 112 can, for example, be configured to provide a substantially flat surface along the scarfed surface of the absorbent web 22. The scarfing roll 112 can optionally be configured to provide a non-flat surface. The scarfing roll 112 is disposed in closely spaced relationship to the forming surface 24, and the forming surface 24 is translated past the scarfing roll 112. A conventional transporting mechanism, such as a suction fan (not shown) can draw the removed fibrous material away from the formed absorbent web 22 and out from the scarfing chamber 110.

In the representatively shown configuration, the scarfing roll 112 rotates in a direction which moves a contacting surface of the scarfing roll 112 in a counter-direction that is opposite the movement direction of the laid absorbent web 22. Alternatively, the scarfing roll 112 may be rotated to provide a co-directional movement of the roller surface relative to the surface of the forming drum 26 most proximate thereto. In either situation, the rotational speed of the scarfing roll 112 should be suitably selected to provide an effective scarfing action against the contacted surface of the formed absorbent web 22. Any other suitable trimming mechanism may be employed in place of the scarfing roll assembly to provide a cutting or abrading action to the laid absorbent web 22 by a relative movement between the absorbent web 22 and the selected trimming mechanism.

After the scarfing operation, the formed absorbent web 22 can be removed from the forming surface 24. In many embodiments, the removal operation may be provided by the weight of the absorbent web 22 and/or by centrifugal force of the drum 26. In some particular embodiments, an optional pressure blow-off zone 77 may further be employed to assist in the removal of the formed absorbent web 22 from the forming surface 24, as is shown in the particular embodiments of FIGS. 1, 2, and 5. For example, the rotation of the forming drum 26 can cause the portion of the forming surface 24 that is carrying the airlaid absorbent web 22 to be moved to pressure blow-off zone 77 of the forming drum 26.

In the blow-off zone 77, air can be introduced under pressure and directed radially outwardly against the absorbent web 22 on the portion of the forming surface 24 that becomes aligned with the blow-off zone 77, as depicted by arrows 98. The gas pressure can affect a ready release of the absorbent web 22 from the forming surface 24, and the absorbent web 22 can be removed from the forming surface 24 onto a suitable transport mechanism.

In some embodiments according to the present disclosure, an air-knife may be used to effectuate the air movement depicted by arrows 98. In these embodiments, the air-knife may be disposed so as to direct air generally perpendicular to forming surface 24. It has been found that air pressures of between about 10 pounds per square inch (psi) and about 40 psi (about 68.9 kPa to about 2,758 kPa) provide the ability to separate the absorbent web 22 from the forming surface 24 without damaging the structural integrity of the formed absorbent web 22. In other embodiments, a preferred range for the air pressures may be between about 10 pounds per square inch (psi) and about 30 psi (about 68.9 kPa to about 2,068 kPa), or between about 15 pounds per square inch (psi) and about 25 psi (about 1,034 kPa to about 1,724 kPa). In different embodiments, an air blower having bullet nozzles may be employed rather than an air-knife. In such embodiments, it has been found that an air pressure of between about 1 psi and about 10 psi (about 6.89 kPa to about 68.9 kPa) provide the ability to separate the absorbent web 22 from the forming surface 24 without damaging the structural integrity of the formed absorbent web 22. In other embodiments, a preferred range for the air pressures may be between about 1 pounds per square inch (psi) and about 7 psi (about 6.89 kPa to about 48.3 kPa), or between about 2 pounds per square inch (psi) and about 6 psi (about 13.8 kPa to about 41.4 kPa).

In still further embodiments, blow-off zone 77 may comprise a region of no air pressure, whether negative (inward into the forming drum 26 through the forming surface 24) or positive (outward through the forming drum 26 and the forming surface 24). In such embodiments, the blow-off zone 77 may act as a vacuum-break zone where a transition occurs from the region of the forming drum 26 comprising the vacuum duct 36 to a region where no air pressure exists. In some embodiments, this region of no negative (or positive) air pressure may result in a clean, consistent release of the formed absorbent web 22 from the forming surface 24.

A web transporter can receive the formed absorbent web 22 from the forming drum 26, and convey the absorbent web 22 for further processing. Suitable web transporters can, for example, include conveyer belts, vacuum drums, transport rollers, electromagnetic suspension conveyors, fluid suspension conveyors or the like, as well as combinations thereof. As representatively shown, the web transporter can be provided by a system which includes an endless conveyor belt 114 disposed about rollers 116.

In a particular configuration of the invention, a vacuum box 118 can be located below the conveyor belt 114 to help remove the absorbent web 22 from the forming surface 24. The vacuum box 118 opens onto the belt 114, and a suction of air out of the vacuum box 118 can draw an air flow through perforations in the conveyor belt 114. This flow of air can, in turn, operate to draw the absorbent web 22 away from the forming surface 24. The vacuum box 118 can be employed with or without the use of a positive pressure in the blow-off zone. The removed absorbent web 22 can provide an interconnected series of pads, and each pad can have a selected surface contour which substantially matches the contour provided by the various, corresponding portions of the forming surface 24 and masking plates 60 upon which each individual pad was formed. Alternatively, the removed absorbent webs 22 may be individual, discrete absorbent webs 22 each spaced from adjacent individual absorbent webs 22.

Accordingly, as described above such absorbent web structures 22 can be formed in a number of different manners. For example, the absorbent web 22 can be formed directly on the forming surface 24 or on a substrate which is disposed directly on the forming surface 24. The absorbent web 22 may be formed as a continuous web structure or as individual, discrete web structures. Different methods to disengage the absorbent web 22 from the forming surface 24 may be employed, such as with or without a blow-off zone 77 and/or utilizing a vacuum box 118 on the web transport configured to receive the formed absorbent web 22 once disengaged from the forming surface 24. Any of these options can be mixed and matched in different embodiments as contemplated herein. In all such embodiments, disengaging the formed absorbent web 22 from the forming surface 24 in a clean and consistent manner can be challenging, particularly at high manufacturing speeds.

Figure 3:
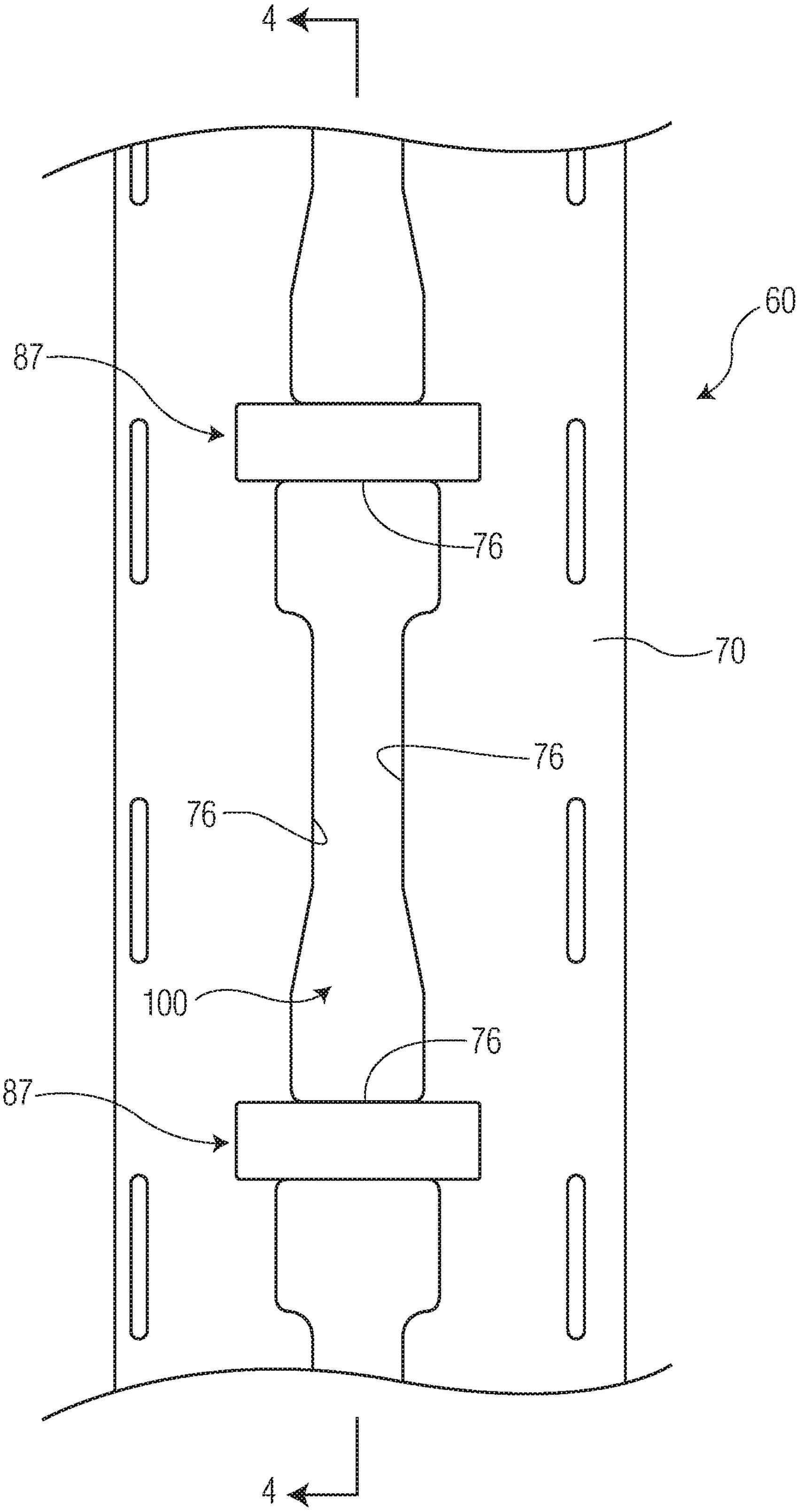
FIG. 3 is a top plan view of a portion of an exemplary masking media, according to aspects of the present disclosure, for use with the forming assembly of FIGS. 1 and 2.
Figure 4:
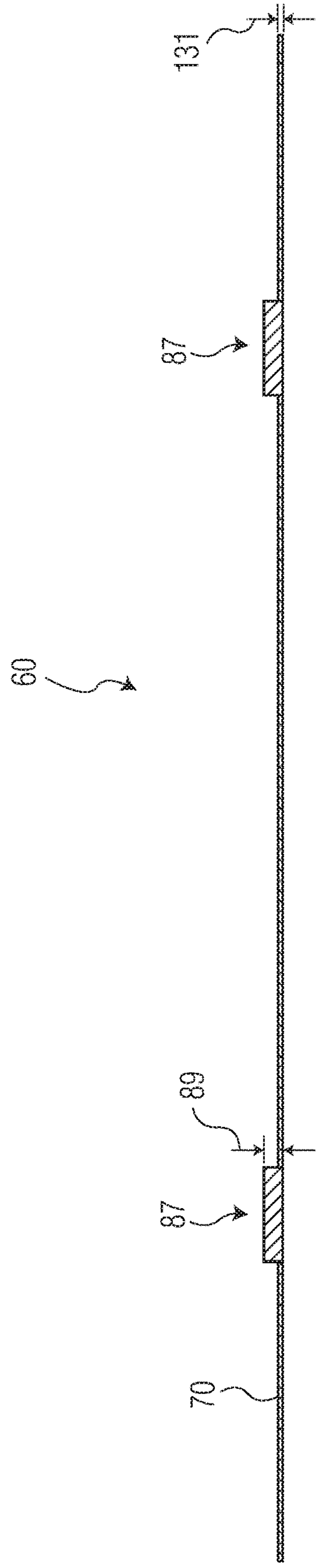
FIG. 4 is a cross-section view of the exemplary masking media of FIG. 3 as viewed along line 4-4.

FIGS. 3 and 4 depict a portion of an exemplary masking media 60 from a top-plan perspective and from a side cross-section perspective, respectively. Employing the masking media 60 of the present disclosure can help to ensure a clean, consistent disengagement of the formed absorbent web 22 from the forming surface 24 in all such embodiments contemplated herein of forming the absorbent web 22. Masking media 60 of the present disclosure generally comprises a thin, as can be seen in FIG. 4, flexible, yet strong material.

The flexibility of the masking media 60 is in contrast to conventional masking media which typically comprise rigid, metal masking plates that attach solidly to the forming drum 26 to cover portions for the forming surface 24. In various embodiments, the masking media 60 can comprise a flexible material having sufficient flexibility to allow the masking media 60 to suck tight to the forming surface 24 such that there is direct contact between the masking media 60 and the forming surface 24 (for example, in a zone of the forming surface 24 corresponding to the vacuum duct 36). When the masking media 60 is sucked tight to the forming surface 24, the absorbent material (such as absorbent fibers) being deposited onto the forming surface 24 within the forming chamber 84 is unable to flow underneath the masking media 60 and become disposed between the forming surface 24 and the masking media 60. Rigid metal masking plates, even when formed according to tight tolerances, can still allow for gaps as large as 0.75 mm to 1.5 mm between the masking plates and the forming surface 24. Such a gap, or even smaller ones, allows for some of the absorbent material in the forming chamber 84 to flow underneath the masking plates. This absorbent material disposed between the masking plates and the forming surface 24 become connected to the larger, formed absorbent web 22 and makes it more challenging to disengage the formed absorbent web or webs 22 from the surface 24 as the connection between the formed absorbent web 22 and the absorbent material disposed between the masking plates and the forming surface 24 needs to be broken.

A few suitable, flexible masking media contemplated by the present disclosure can those formed from a variety of polymeric materials, such as low-density polyethylene (LDPE), high-density polyethylene (HDPE), polyethylene terephthalate (PET), polyethylene terephthalate glycol (PETG), polypropylene (PP), polyester, polyvinyl chloride (PVC), polystyrene (PS), nylon, teflon (polytetrafluoroethylene), thermoplastic polyurethanes (TPU), polylactic acid (PLA), polycarbonate, and/or any combinations or derivatives of such materials. Various epoxy materials may also be used to form suitable flexible materials for use as masking media 60. Still further materials may be suitable for forming the masking media 60 include any rubber based materials and foam and/or sponge materials. It should be understood that the above referenced materials are not an exhaustive list of materials contemplated for use as masking media 60 by the present disclosure. In general, any material may be chosen to form the masking media 60 that has sufficient flexibility to suck tight to and form direct contact with the forming surface 24.

In at least some embodiments, the masking media 60 may comprise one or more metallic components. For example, the material of which the masking media 60 is made may comprise between about 5% to about 25%, by weight, of iron or another component that displays a type of magnetism (e.g. ferro- or ferri-magnatism, or possibly paramagnetism or diamagnetism) detectable in a production process. For safety considerations, it may be desirable to be able to detect if pieces or portions of the masking media 60 end up in the formed absorbent web 22. By employing iron, or another material detectable with magnetic sensors, formed absorbent webs 22 (and garments comprising such formed absorbent webs 22) can be detected which contain such pieces or portions of the masking media 60 and removed from production, typically prior to packaging in a box for sale.

Another feature of the masking media 60 that can help to ensure clean, consistent disengagement of the formed absorbent web 22 from the forming surface 24 is when the masking media 60 is thin. For example, the absorbent material deposits onto the forming surface 24 between the inboard side edges 76 of the masking media 60 and builds up a thickness of the absorbent web 22 as the web 22 is being formed. In the resulting formed absorbent web 22, side edges of the formed absorbent web 22 abut the inboard side edges 76 of the masking media 60. If the masking media 60 has a thickness 131 (as shown in FIG. 4) that is too great, friction between side edges of the absorbent web 22 and the inboard side edges 76 of the masking media 60 can make it difficult to dislodge the formed absorbent web 22 from the forming surface 24. It has been found that may be most beneficial for the masking media 60 to have a thickness 131 of between about 0.1 mm and about 7 mm. In more specific of these embodiments, the masking media 60 may have a thickness 131 that is between about 0.1 mm and about 5 mm, or between about 0.1 mm and about 2.5 mm, or between about 0.1 mm and about 1 mm. These values for height 131 are generally useful for formed absorbent fibrous webs having thicknesses of between about 2.5 mm and about 15 mm. For absorbent fibrous webs having greater or less thicknesses, the disclosed values for thickness 131 could be adjusted so as to retain the same proportionality with respect to the greater or lesser fibrous web heights.

In some embodiments, these flexible and thin properties may allow for the formed absorbent web 22 to cleanly and consistently release from the forming surface 24 when the blow-off zone 77 is configured to provide no positive or negative air pressure through the forming surface 24. In these embodiments, the friction between the formed absorbent web 22 and the masking media 60 may be low enough that the centrifugal forces acting on the formed absorbent web 22 are sufficient to disengage the formed absorbent web 22 from the forming surface 24 once the formed absorbent web 22 has moved beyond the region of the forming drum 26 having the vacuum duct 36 where the formed absorbent web 22 is held to the forming drum 26 through vacuum pressure.

In further embodiments, however, centrifugal forces may not be enough to cleanly and consistently disengage the formed absorbent web 22 from the forming surface 24. For example, the specific material and/or thickness of the masking media 60, or the composition of the formed absorbent web 22 may not readily allow for clean, consistent disengagement from the forming surface 24 where no positive air pressure is provided through the blow-off zone 77. Accordingly, as described previously, the forming drum 26 may comprise an air-knife or other air-blower configured at particular air-pressures to provide airflow through the forming surface 24 within the blow-off zone 77.

In at least some of these embodiments where positive air pressure through the forming surface 24 is provided within the blow-off zone 77, the masking media 60 may be configured to be flexible enough such that the masking media 60 flexes away from the forming surface 24 when disposed over the blow-off zone 77. In such embodiments, as the masking media 60 enters the blow-off zone 77, the positive air pressure through and out of the forming drum 26 and the forming surface 24 in this zone 77 can cause the masking media 60 to flex away from the forming surface 24, providing a gap between the masking media 60 and the forming surface 24. As the masking media 60 flexes away from the forming surface 24 in such embodiments, the masking media 60 helps the formed absorbent web 22 to disengage from the forming surface 24. For example, the fibers and (and optionally superabsorbent particles) of the formed absorbent web 22 abut the inboard side edges 76 of the masking media 60. As the masking media 60 flexes away from the forming surface 24, friction between the formed absorbent web 22 and the inboard side edges 76 of the masking media 60 can help to pull the formed absorbent web 22 away from the forming surface 24.

Figure 5:
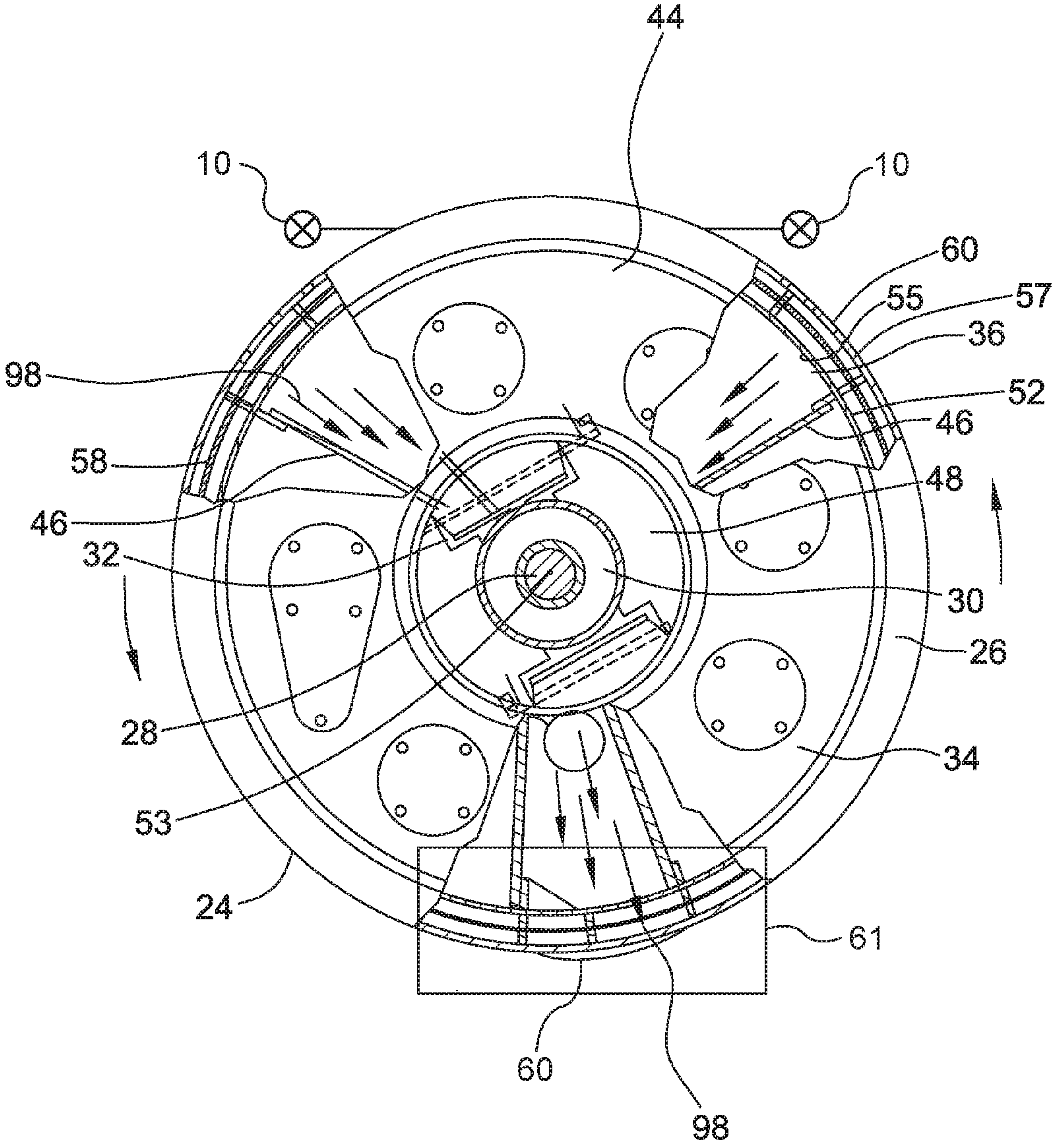
FIG. 5 is a side view of a forming drum of the forming assembly of FIG. 1 further illustrating an exemplary masking media according to aspects of the present disclosure.
Figure 6:
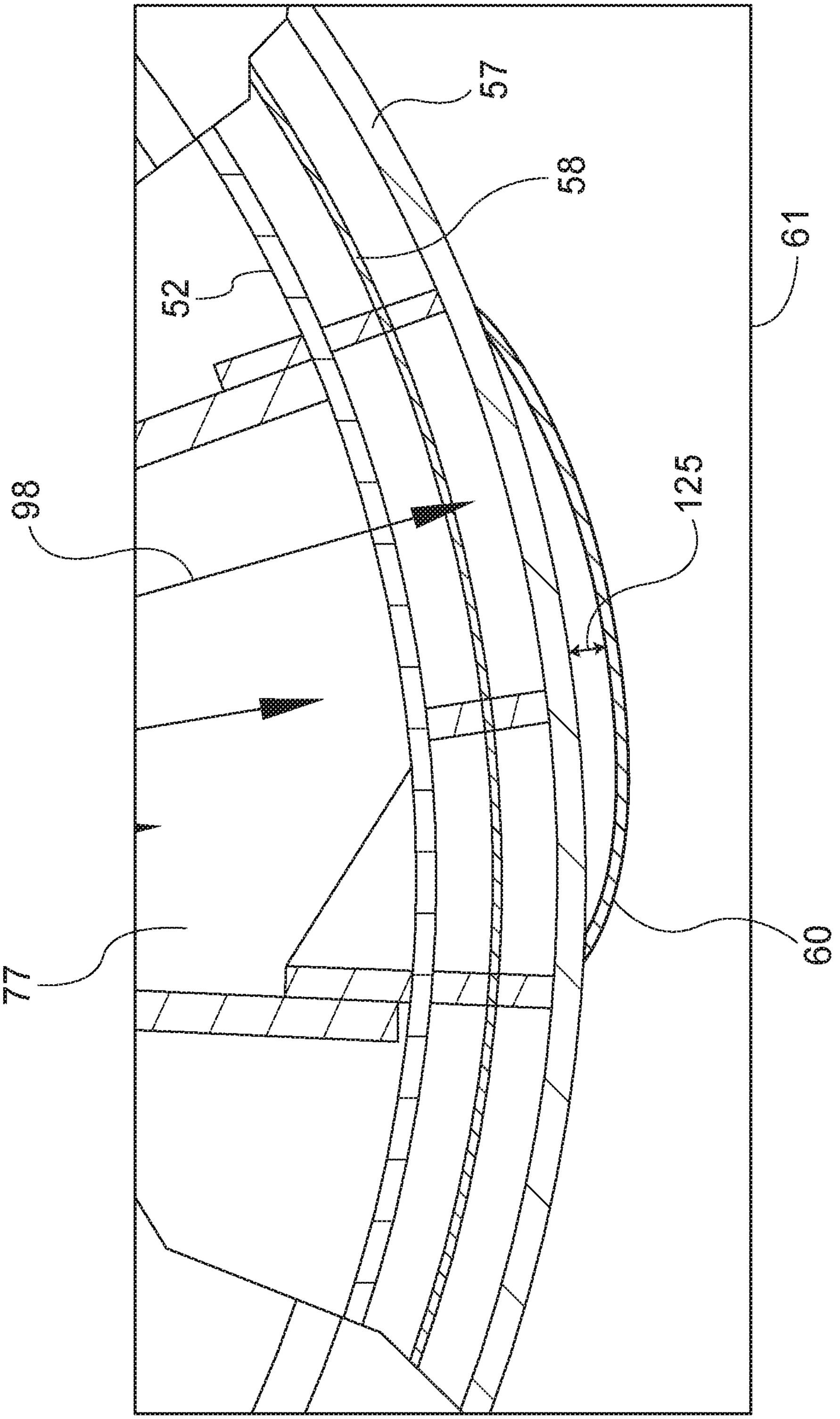
FIG. 6 is a close-up of a portion of the forming drum of FIG. 5 further illustrating an exemplary masking media according to aspects of the present disclosure.
Figure 7:
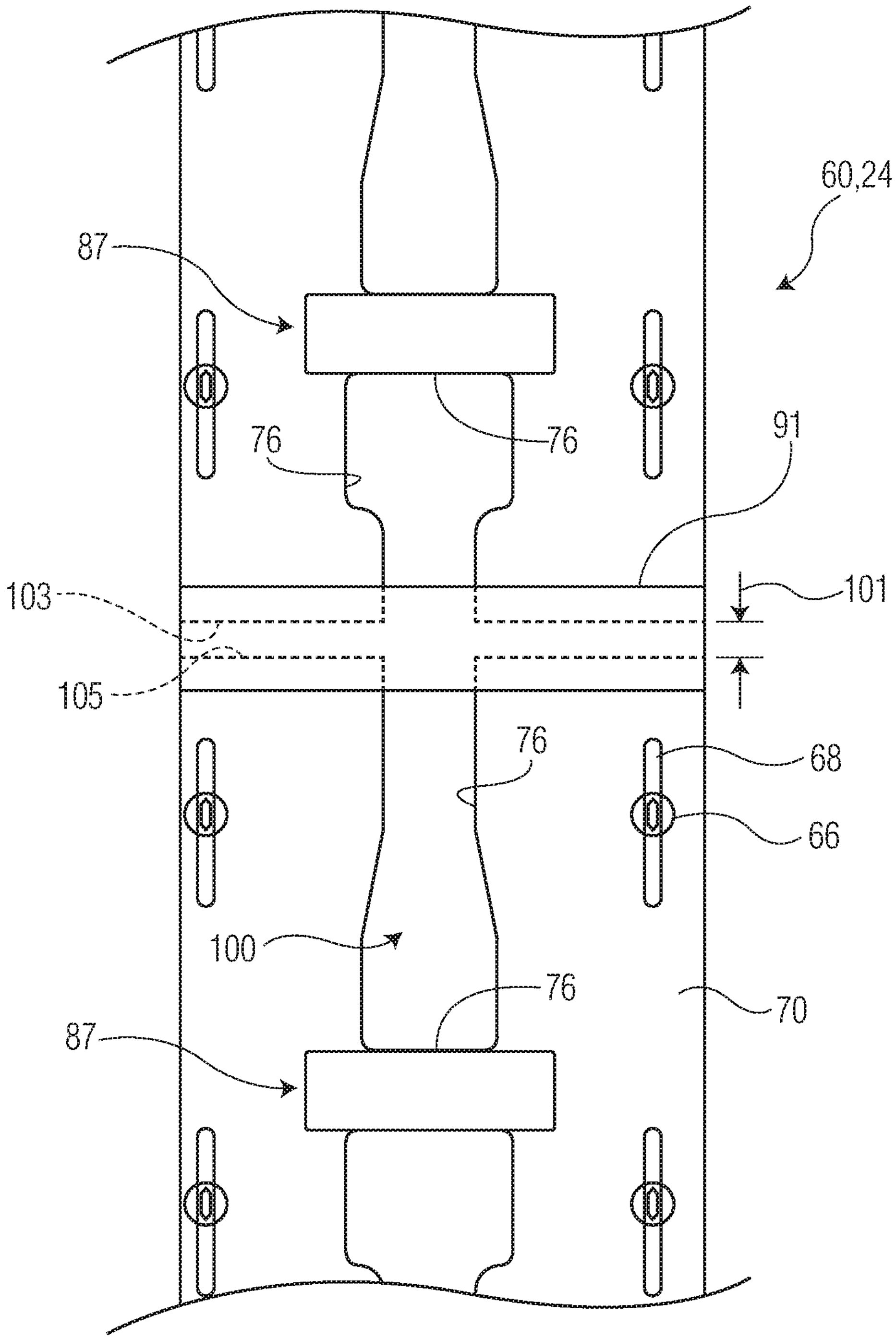
FIG. 7 is a top-plan view of the forming drum of FIG. 5 depicting and exemplary masking media according to aspects of the present disclosure.

Such embodiments where the masking media 60 flexes away from the forming surface 24 can be seen in FIGS. 5 and 6. FIG. 5 depicts the forming drum 26 in isolation from the rest of the forming apparatus 20 and the absorbent web 22 to more clearly see the flexing action of the masking media 60. FIG. 6 is a close-up of box 61 depicting the blow-off zone 77 where the gap 125 between the masking media 60 and the forming surface 24 in the blow-off zone 77 can be more clearly seen. In general, the flexing of the masking media 60 away from the forming surface 24 does not need to result in a large gap 125 to result in clean, consistent disengagement of the absorbent web 22 from the forming surface 24. For instance, the gap 125 may only need to be greater than about 0.25 mm in some embodiments. In other embodiments, it may be beneficial for the gap to be greater than about 0.5 mm, or greater than about 0.75 mm, or greater than about 1.0 mm, or greater than about 1.5 mm, or greater than about 2.0 mm, or greater than about 3.0

Another optional beneficial feature of the masking media 60 is that it may be a strong material. More specifically, it may be desirable for the masking media 60 to maintain its integrity for a high number of forming cycles. One forming cycle is defined as one traversal around the forming apparatus. For example, in the embodiment of FIGS. 1 and 2, one forming cycle would comprise one full revolution of the forming drum 26. Accordingly, it may be beneficial for the masking media 60 to last for at least 500,000 forming cycles. In more specific embodiments, it may be beneficial for the masking media 60 to last for at least 1,000,000 forming cycles, or at least 5,000,000 forming cycles, or at least 10,000,000 forming cycles in other embodiments. Materials having such described strength may represent a beneficial trade-off over using traditional metal masking plates, as the masking media 60 of the present disclosure would need to be replaced infrequently enough, although still more frequently than traditional metal masking plates, for their benefits to be outweighed by the increased replacement frequency.

Still another optional feature of the masking media 60 is a region of increased thickness 87. In some embodiments, it may be desirable to form a very distinct front and/or rear edge of the formed absorbent web 22 when forming individual, discrete absorbent webs 22. For example, front and/or rear edges of absorbent cores (which are formed from such absorbent fibrous web structures 22) are sometimes detected optically for use as a marker for registering printed graphics within an individual absorbent article, or for identifying a location to cut a connected series of absorbent articles into individual absorbent articles, or the like in an absorbent article manufacturing operation. In such embodiments, one method to ensure a very distinct front and/or rear edge of the formed absorbent web 22 is to employ a region of increased thickness 87 of the masking media 60 directly adjacent the front and/or rear inboard side edges 76. This a region of increased thickness 87 may prevent any (or fewer) absorbent fibers and/or particles from overlaying the front and/or rear inboard side edges 76 masking media 60 during formation. In circumstances where some absorbent fibers and/or particles do overlay the front and/or rear inboard side edges 76 masking media 60, the resulting formed absorbent web 22 will have extended, lower-basis weight front and/or rear 'zones' rather than clean, distinct front and/or rear edges.

FIGS. 3 and 4 depict masking media 60 having such a region of increased thickness 87. Region 87 has a thickness 89 that may be between about three times and about twenty times the thickness 131 of the masking media 60. In more specific embodiments, the thickness 89 may be between about three times and about fifteen times, or between about three times and about ten times, or between about three times and about eight times, the thickness 131 of the masking media 60. It should be understood that the region 87 is not required in all contemplated embodiments. In some forming processes, the region 87 may not be required or desired.

Figure 8:
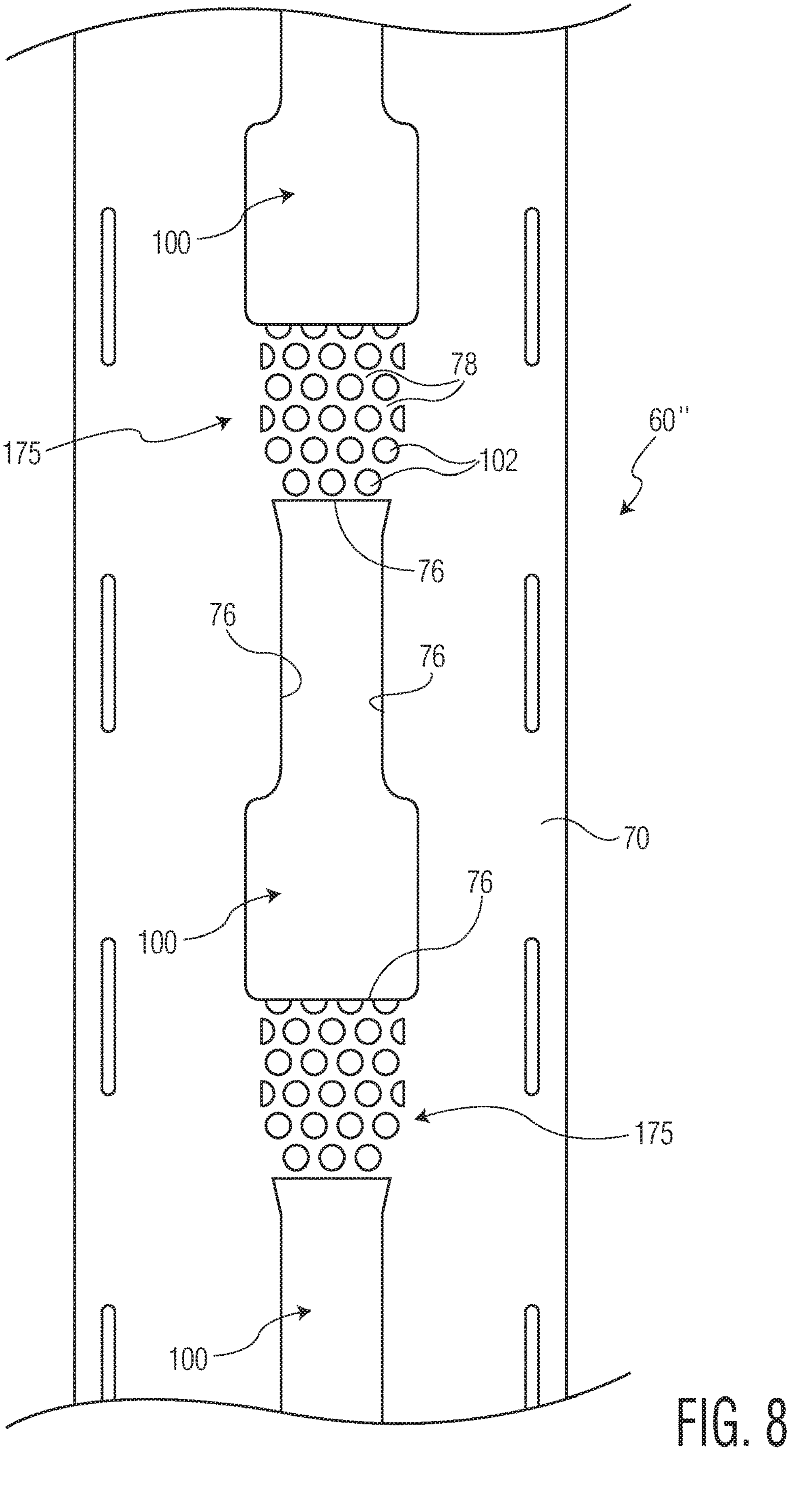
FIG. 8 is a top-plan view of another exemplary masking media according to aspects of the present disclosure.

FIG. 8 depicts a top plan view of the forming drum 26 with the masking media 60 disposed thereon. In some embodiments, the masking media 60 may comprise one continuous belt-like segment that is wrapped around the forming drum 26. In such embodiments, the masking media 60 may have a first end 103 and a second end 105. The first end 103 and the second end 105 may abut each other when the masking media 60 is wrapped around the circumference of the forming surface 24.

In some embodiments, a length of the masking media 60 may be substantially equal to the circumference of the forming surface 24. In other embodiments, the masking media 60 may have a length that is somewhat less than the outer circumference of the forming surface 24. In such embodiments, a small gap 101 may be located between the ends 103, 105 of the masking media 60 when placed on the forming surface 24. In various embodiments, the gap 101 may be between about 0 mm and about 30 mm. Although the ends 103, 105 are shown as forming a break in one of the open areas 100 of the masking media 60, it should be understood that the masking media 60 can be formed so the ends 103, 105 form a break between any portion of the masking media 60, for instance between the open areas 100, at one of the front or rear end inboard side edges 76, or anywhere else. In some particular embodiments, it has been found that a length of the masking media 60 can be equal to an outer circumference of the forming surface 24, plus two times a thickness of the masking media 60, and minus between about 0.05 mm and about 0.25 mm. In general, the end 103, 105 of the masking media 60 should not overlap each other. In general, the masking media 60 may be substantially in-extensible along a long-dimension of the masking media 60.

An additional connecting portion 91 may be employed in some embodiments to be disposed over the abutting ends 103, 105 of the masking media 60 when placed on the forming surface 24, as shown in FIG. 8. The connecting portion 91 may be used in embodiments where there is a gap 101 or where there is no gap 101 such that the ends 103, 105 directly abut each other. The connecting portion 91 may be placed on top of the masking media 60 so as to cover the ends 103, 105, thereby preventing any material, such as absorbent fibers or superabsorbent particles, from entering the gap 101 or between the ends 103, 105 where the ends 103, 105 directly abut each other. The connecting portion 91 may generally be thin and flexible. The connecting portion 91 may preferably have adhesive disposed on one side for easy attachment to the masking media 60, such as any of a number of suitable tape materials, for example.

In further embodiments, the masking media 60 may be formed from multiple individual segments. In these embodiments, each individual segment may be placed onto the forming surface 24 such that there is a gap 101, or such that the ends of the individual segments of the masking media 60 directly abut each other. In such embodiments, multiple connecting portions 91 may be employed to span between each pair of adjacent individual sections of the masking media 60.

In some embodiments, the masking media 60 may be connected to the forming drum 26 by a plurality of bolts 66 inserted through holes 68 in the masking media 60 and the forming surface 24. In other embodiments, one or more brackets (not shown) may be placed over the masking media 60 and connected to the forming surface 24, thereby sandwiching the masking media 60 between the bracket and the forming surface 24. In some of these embodiments, only a single bracket may be employed which spans across the ends 103, 105 of the masking media 60. In such embodiments, the rest of the masking media 60 may be secured to the forming drum 26 through the plurality of bolts 66. In other embodiments, multiple brackets may be placed around the whole circumference of the forming drum 26.

FIGS. 3 and 4 depict the exemplary masking media 60 in an embodiment where the masking media 60 includes individual, unconnected open areas 100. Accordingly, in the embodiment shown in FIGS. 3 and 4, the depicted masking media 60 may be suitable for forming individual, discrete absorbent fibrous web structures 22. However, this is only one contemplated embodiment. FIG. 8 depicts a portion of an alternative embodiment of a masking media contemplated by the present disclosure, masking media 60', which has one continuous, connected open area 100, interspersed with zoning regions 175. Similar to the embodiment of FIGS. 3 and 4, the masking media 60' still comprises contoured inboard side edges 76. Accordingly, masking media 60' may be suitable for forming a continuous length absorbent web structure 22.

Zoning regions 175 operate to displace at least some of the absorbent material within the one or more zoning regions 175 toward the open area 100 to create one or more lower basis weight regions within the formed absorbent web 22. For example, the zoning regions 175 comprise one or more masking portions 78 which are disposed in a same general region of the masking media 60" as the open area 100 and define one or more open geometric areas 102. The masking portions 78 at least partially inhibit deposition of absorbent material in the zoning regions 175 and, therefore, displace the absorbent material to the open areas 100. As a result, the zoning regions 175 will form portions of the absorbent web 22 that have lower basis weights than the portions of the absorbent web 22 formed by the open areas 100. Accordingly, the masking media 60' of FIG. 8 would produce a continuous length of an absorbent fibrous web structure 22, with portions of the absorbent web structure 22 having regions of lower basis weight. Preferably, the masking portions 78 cover between about 20% and about 75% of a zoning region 175. More preferably, the masking portions 78 cover between about 20% and about 40% of a zoning region 175.

The masking portions 78 may have any suitable shape and combinations of shapes, e.g., without limitation, curved and/or straight shapes. Moreover, the masking portions 78 may have any size. Preferably, each masking portion 78 has a width that is less than 1 cm and, even more preferably, has a width that is less than 0.5 cm. The masking portions 78 may define geometric areas 102 which have any suitable shapes, such as polygons, squares, triangles, trapezoids, and/or circles. Preferably, each geometric area 102 has an area between about 10 square millimeters (mm2) and about 2,500 mm2. More preferably, each geometric area 102 has an area between about 25 mm2 and about 2,000 mm2. Even more preferably, each geometric area 102 has an area between about 100 mm2 and about 1,000 mm2. In one preferred embodiment, each of the geometric areas 102 have a circular shape with overall widths of between 5 and 50 mm.

In some embodiments, at least some of the masking portions 78 and geometric areas 102 are offset from bordering masking portions 78 and geometric areas 102. It is believed that this offset configuration may facilitate forming a stronger absorbent web 22. In some embodiments, a minimum distance between each geometric area 102 may be between about 3 mm and about 10 mm to help maintain integrity of the resulting formed absorbent web 22.

Figure 9:
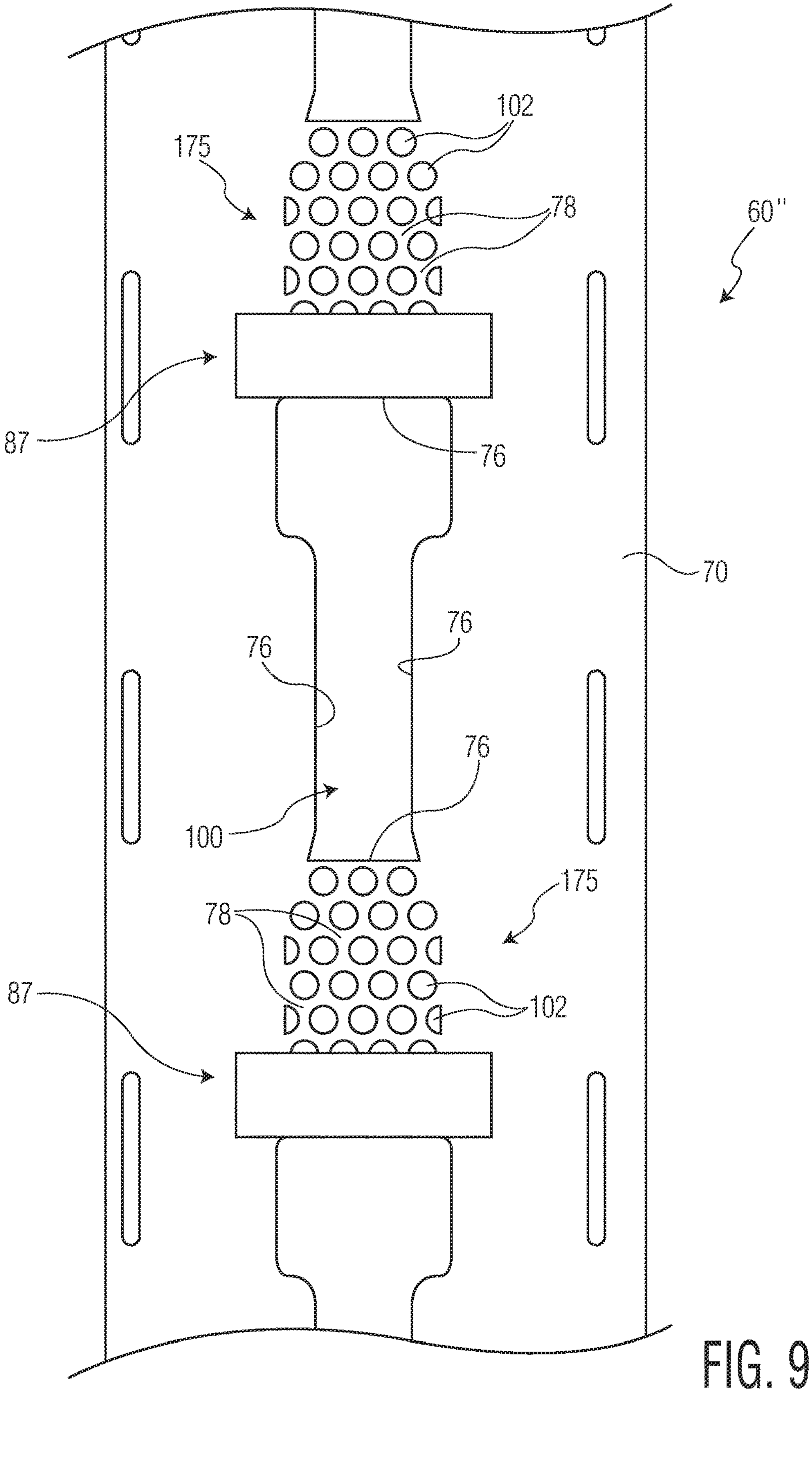
FIG. 9 is a top-plan view of a further exemplary masking media according to aspects of the present disclosure.

FIG. 9 depicts a portion of a further exemplary embodiment of a masking media according to the present disclosure, masking media 60". In the embodiment of FIG. 9, the masking media 60" may have one or more zoning regions 175 while having separate, discrete open areas 100. Accordingly, the masking media 60" allows for formation of individual, discrete absorbent fibrous web structures 22 where each of the individual, discrete absorbent fibrous web structures 22 comprises a lower basis weight region. In the embodiment of FIG. 9, the masking media 60" may include regions of increased thickness 87 to help create clear, distinct front and/or rear edges of the individual, discrete absorbent web structures 22, as described previously. However, it should be understood that this is an optional feature which may not be present in all contemplated embodiments.

Figure 10:
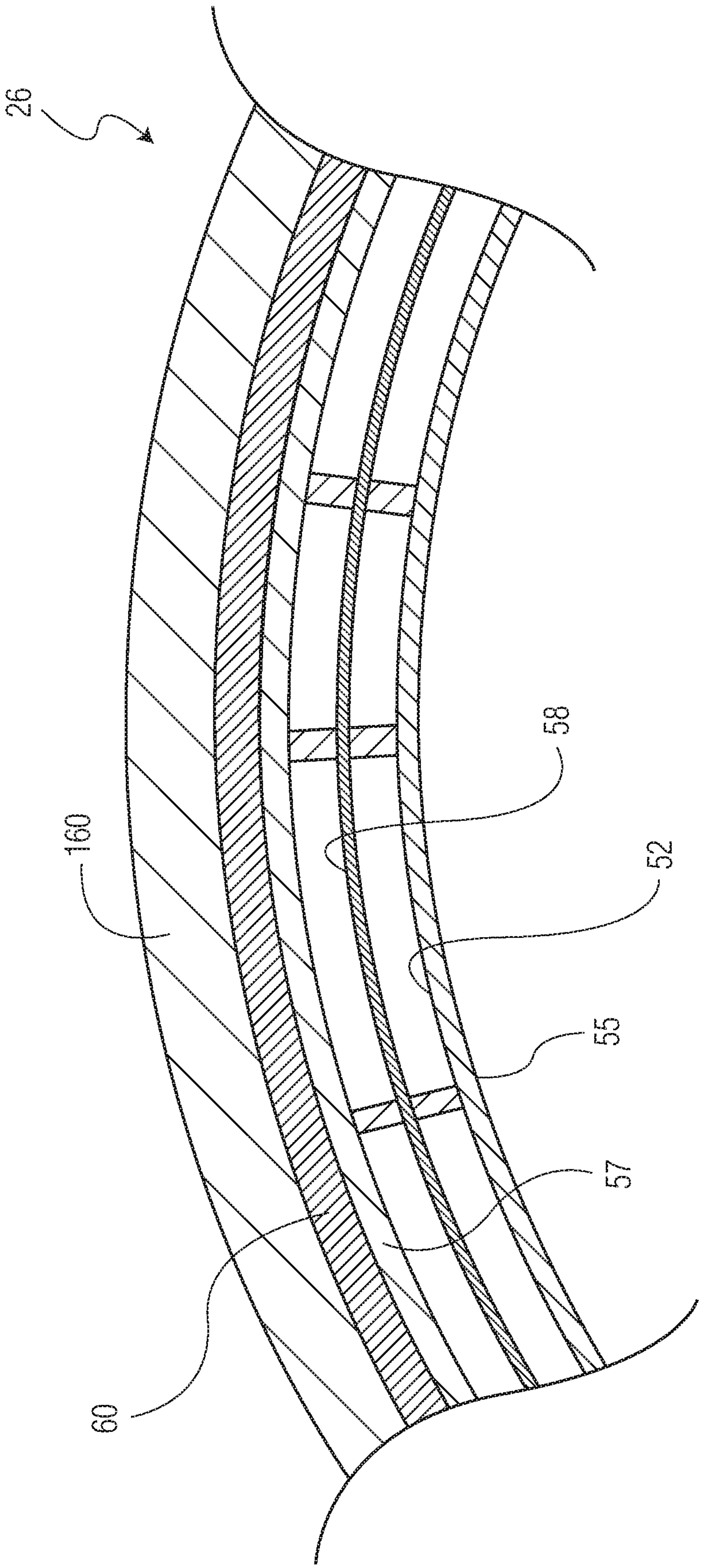
FIG. 10 is a cross-section of the forming drum of FIG. 5 as viewed along a plane parallel to line 10-10.

In another embodiment according to the present disclosure, the masking media 60 described herein may be used in conjunction with a traditional, metal masking plate. FIG. 10 depicts an exemplary portion of a cross-section of the forming drum 26 of FIG. 5 as viewed along a plane parallel to line 10-10 depicting a configuration where the forming drum 26 includes both masking media 60 along with traditional masking plate 160. As can be seen, in this configuration, masking media 60 is disposed most proximate the forming surface 24 so as to be in direct contact with the forming surface 24. The masking plate 160 is disposed over the masking media 60 so as to sandwich the masking media 60 between the masking plate 160 and the forming surface 24. This sandwich configuration provides the benefits of the masking media 60 with the durability benefits of the traditional masking plate 160. For example, the masking plate 160 may be formed from any suitable metal or metal alloy, such as aluminum, iron, or steel. With the masking plate 160 overlaying the masking media 60, the masking plate 160 protects the masking media 60 from the processing environment to provide for a longer life of the masking media 60. The masking media 60 still provides the benefits described herein, such as sucking tight to the forming surface 24 in the vacuum region 36 and preventing absorbent material from flowing between the masking plate 160 and the forming surface 24. Accordingly, the benefits that masking media 60 provide in relation to removal of the formed absorbent web 22 are retained in these embodiments. The masking plate 160 may have open areas corresponding substantially to the open areas 100 and/or 102 of the masking media 60.

Figure 11:
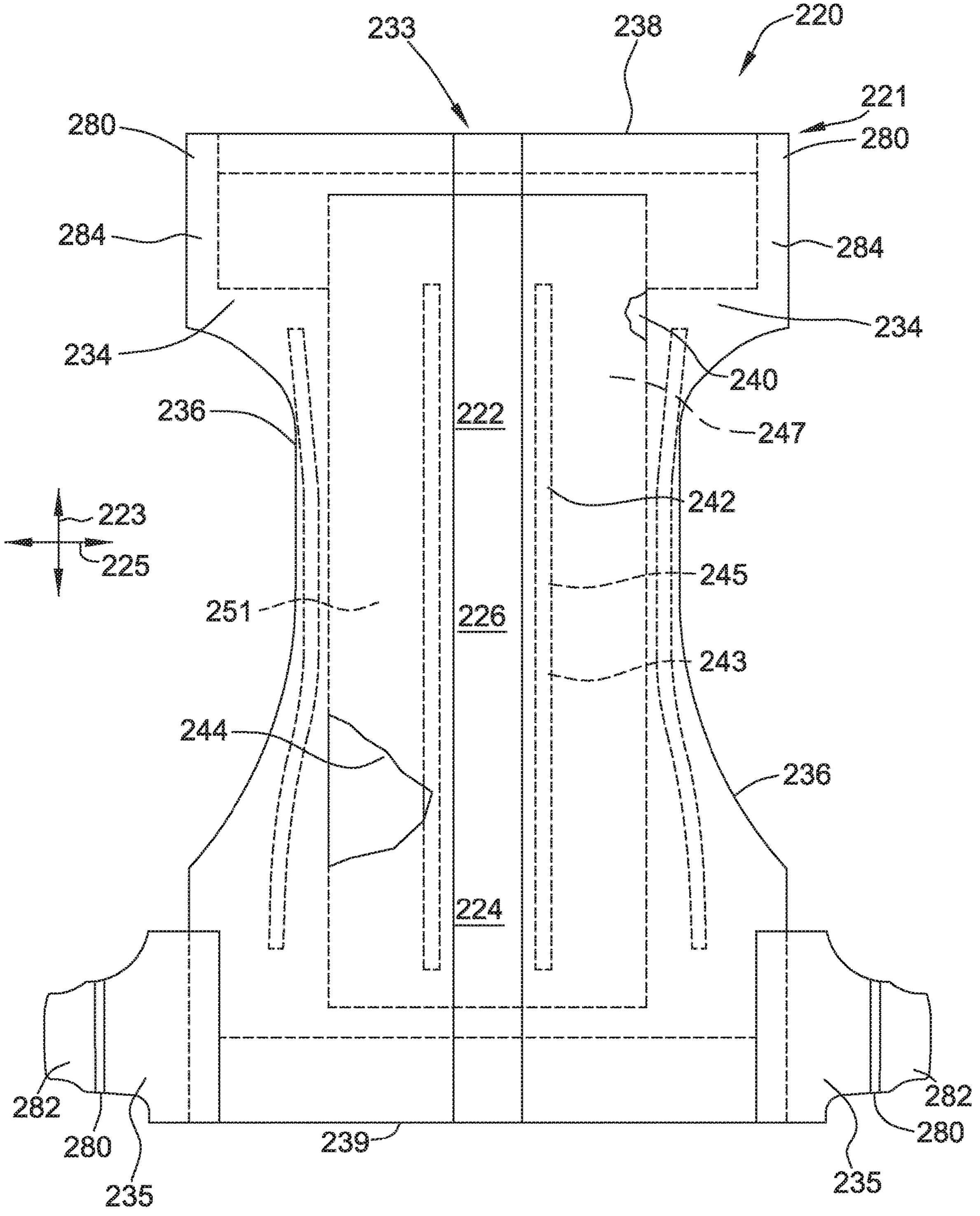
FIG. 11 is top plan view of an absorbent article incorporating one suitable embodiment of a bridged absorbent structure, the absorbent article being illustrated in a laid flat configuration.

FIG. 11 shows an example absorbent article including an absorbent structure manufactured according to aspects of the present disclosure. The exemplary absorbent article is in the form of a diaper 220 illustrated in an unfastened, unfolded and laid-flat condition. The diaper 220 comprises a chassis 221, having a generally rectangular center panel 233, a pair of laterally opposite front side ears 234, and a pair of laterally opposite back side ears 235. For reference, arrows 223 and 225 depict the orientation of the longitudinal axis 223 and the transverse or lateral axis 225, respectively, of the diaper 220. It is contemplated that the absorbent article can have other forms without departing from some aspects of this invention (e.g., a training pant and incontinence article).

The center panel 233 of the diaper 220 is configured to contain and/or absorb exudates released by a wearer of the diaper 220. As seen in FIG. 11, the center panel 233 has a front waist region 222, a back waist region 224, and a crotch region 226 extending between and interconnecting the front and back waist regions 222, 224. The center panel 233 further includes a pair of side edges 236, a front waist edge 238, and back waist edge 239. The center panel 233 and side ears 234, 235 may comprise separate elements or be integrally formed.

The illustrated center panel 233 comprises an outer cover 240, a body-side liner 242, and an absorbent structure 244 disposed between the outer cover 240 and the body-side liner 242. In one suitable embodiment, the outer cover 240 comprises a material that is substantially liquid impermeable, and can be elastic, stretchable, or nonstretchable. The outer cover 240 can be a single layer of liquid impermeable material, but suitably comprises a multi-layered laminate structure in which at least one of the layers is liquid impermeable. For instance, the outer cover 240 can include a liquid permeable outer layer and a liquid impermeable inner layer that are joined together by a laminate adhesive, ultrasonic bonds, thermal bonds, or the like. Suitable laminate adhesives can be applied continuously or intermittently as beads, a spray, parallel swirls, or the like. The liquid permeable outer layer can be any suitable material and desirably one that provides a generally cloth-like texture. The inner layer of the outer cover 240 can be both liquid and vapor impermeable, or can be liquid impermeable and vapor permeable. The inner layer can be manufactured from a thin plastic film, although other flexible liquid impermeable materials may also be used. The inner layer, or the liquid impermeable outer cover 240 when a single layer, inhibits liquid exudates from wetting articles, such as bed sheets and clothing, as well as the wearer and caregiver.

The body-side liner 242 is liquid permeable and overlies the absorbent structure 244 and outer cover 240. In one suitable embodiment, a width of the body-side liner 242 is less than the width of the outer cover 240. It is understood, however, that the body-side liner 242 and the outer cover 240 can have dimensions other than those illustrated herein. For example, the body-side liner 242 and the outer cover 240 can have substantially the same dimension or the body-side liner 242 can be wider than the outer cover 240.

The body-side liner 242 suitably presents a body facing surface of the diaper 220, which is compliant, soft feeling, and non-irritating to the wearer's skin. Further, the body-side liner 242 may be less hydrophilic than the absorbent structure 244, to present a relatively dry surface to the wearer, and may be sufficiently porous to be liquid permeable, permitting liquid to readily penetrate through its thickness. A suitable body-side liner 242 may be manufactured from a wide selection of web materials, such as porous foams, reticulated foams, apertured plastic films, natural fibers (i.e., wood or cotton fibers), synthetic fibers (i.e., polyester or polypropylene fibers), or a combination of natural and synthetic fibers. Various woven and nonwoven fabrics can be used for the body-side liner 242. For example, the body-side liner 242 can be composed of a meltblown or spunbonded web of polyolefin fibers. The body-side liner 242 can also be a bonded-carded web composed of natural and/or synthetic fibers. The body-side liner 242 can be composed of a substantially hydrophobic material, and the hydrophobic material can, optionally, be treated with a surfactant or otherwise processed to impart a desired level of wettability and hydrophilicity. In one suitable embodiment, for example, the body-side liner 242 can be a hydrophobic three-layer nonwoven polypropylene material known as SMS. SMS is an acronym for Spunbond, Meltblown, Spunbond, the process by which the three layers are constructed and then laminated together. One example of an SMS material is described in U.S. Pat. No. 4,041,203 to Brock et al. The body-side liner 242 is suitably employed to help isolate the wearer's skin from liquids held in the absorbent structure 244.

The absorbent structure 244 is generally compressible, conformable, non-irritating to the wearer's skin, and capable of absorbing and retaining liquids and certain body wastes, and may be manufactured in a wide variety of sizes and shapes, and from a wide variety of liquid absorbent materials commonly used in the art. In at least some embodiments, the absorbent structure 244 is formed according to aspects of the present disclosure. The exemplary absorbent structure 244 includes a layer 243 of fibrous material having areas of high basis weight and areas of low basis weight. In suitable embodiments, a wrapsheet 251 is wrapped about at least one face of the absorbent structure 244. In the illustrated embodiment, the wrapsheet 251 suitably covers the body-side face (i.e., that faces the wearer when the absorbent article is worn), the side edges, and a portion of the garment side face of the absorbent structure 244.

The center panel 233 can also incorporate other materials designed primarily to receive, temporarily store, and/or transport liquid along the mutually facing surface with absorbent structure 244, thereby maximizing the absorbent capacity of the absorbent assembly. One suitable material is referred to as a surge management layer (not shown) and may be located between the absorbent assembly and the body-side liner 242. The surge management layer helps to decelerate and diffuse surges or gushes of liquid that may be rapidly introduced into the absorbent structure 244. The surge management layer can rapidly accept and temporarily hold the liquid prior to releasing the liquid into the storage or retention portions of the absorbent structure 244. Examples of suitable surge management layers are described in U.S. Pat. Nos. 5,486,166 and 5,490,846. Other suitable surge management materials are described in U.S. Pat. No. 5,820,973.

As seen in FIG. 11, the front and back side ears 234, 235 are disposed on laterally opposite sides of the center panel 233 in longitudinally spaced relationship with each other. In the illustrated embodiment, the back side ears 235 are permanently bonded along seams to the center panel 233 in the respective back waist region 224. More specifically, each of the back side ears 235 are sandwiched between the outer cover 240 and the body-side liner 242 permanently bonded to both the outer cover and the body-side liner 242. The front side ears 234 are integrally formed with the center panel 233. The front side ears 234 extend transversely outward beyond the side edges 236 of the center panel 233 in the front waist region 222, and the back side ears 235 extend transversely outward beyond the side edges 236 of the central panel 233 in the back waist region 224.

In suitable embodiments, the front and back side ears 234, 235 may be bonded to the center panel 233 using any attachment means known to those skilled in the art such as adhesive, thermal or ultrasonic bonding. In the illustrated embodiment, for example, the back side ears 235 are adhesively bonded to both the outer cover 240 and the body-side liner 242. As mentioned above, the front and back side ears 234, 235 can be formed as an integral portion of a component of the center panel 233. For example, the front and back side ears 234, 235 can comprise a generally wider portion of the outer cover 240 and/or the body-side liner 242.

In one suitable embodiment, the front and back side ears 234, 235 comprise an elastic material capable of stretching in a direction generally parallel to the transverse axis 225 of the diaper 220. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al. Alternatively, the side panel material may comprise other woven or nonwoven materials, such as those described above as being suitable for the outer cover 240 or body-side liner 242, mechanically pre-strained composites, or stretchable but inelastic materials.

The illustrated diaper 220 includes a fastening system 280 for refastenably securing the diaper 220 about a waist of the wearer. The illustrated fastening system 280 includes first fastening components 284 adapted for refastenable engagement to corresponding second fastening components 282. In the illustrated embodiment, the first fastening components 284 comprise a plurality of projecting engaging elements. The engaging elements of the first fastening components 284 are adapted to repeatedly engage and disengage engaging elements of the second fastening components 282.

The fastening components 284, 282 can comprise separate elements bonded to the side ears 234, 235, or they may be integrally formed with the side ears 234, 235. In the illustrated embodiment, for example, the first fastening components 284 are formed separate from the front side ears 234 and bonded thereto. The second fastening components 282, on the other hand, are integrally formed with the back side ears 235. The first fastening components 284 can be bonded to the respective front side ears 234 by any means known to those skilled in the art such as adhesive bonds, ultrasonic bonds or thermal bonds.

The fastening components 284, 282 can comprise any refastenable fasteners suitable for absorbent articles, such as adhesive fasteners, cohesive fasteners, mechanical fasteners, or the like. In the illustrated embodiment, the fastening components 284, 282 comprise mechanical fastening elements. Suitable mechanical fastening elements can be provided by interlocking geometric shaped materials, such as hooks, loops, bulbs, mushrooms, arrowheads, balls on stems, male and female mating components, buckles, snaps, or the like.

Figure 12:
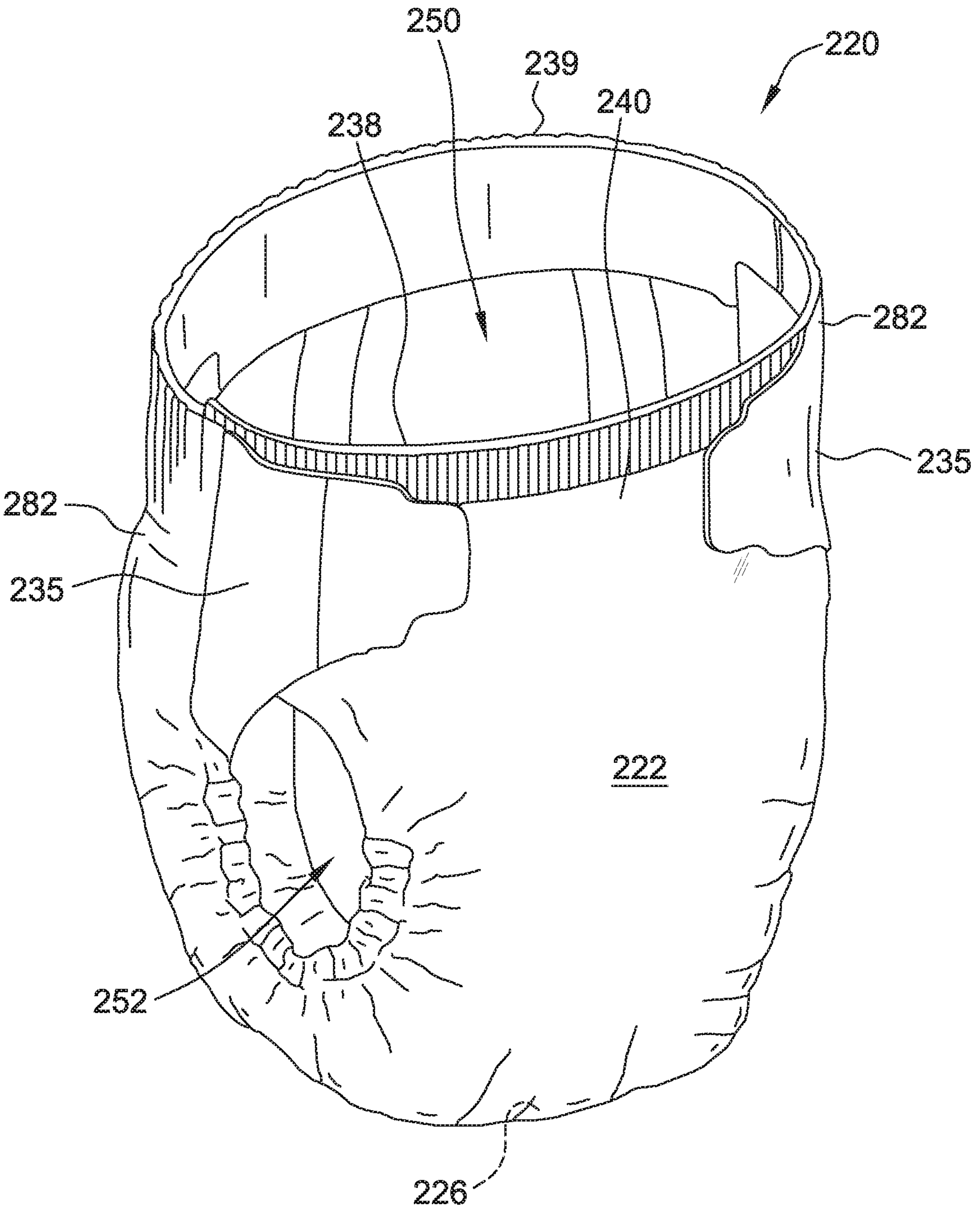
FIG. 12 is a perspective view of the absorbent article of FIG. 11, the absorbent article being illustrated in a use configuration.

In a ready-to-wear, three dimensional configuration of the diaper 220, which is illustrated in FIG. 12, the front and back side ears 234, 235 are secured together to define a three-dimensional wear configuration having a waist opening 250 and a pair of leg openings 252. The front waist region 222 comprises the portion of the diaper which, when worn, is positioned on the front of the wearer while the back waist region 224 comprises the portion of the diaper which, when worn, is positioned on the back of the wearer. The crotch region 226 of the diaper 220 comprises the portion of the diaper which, when worn, is positioned between the legs of the wearer and covers the lower torso of the wearer. The front and back side ears 234, 235 define the portions of the diaper 220 which, when worn, are positioned on the hips of the wearer. The waist edges 238, 239 of the diaper chassis 221 are configured to encircle the waist of the wearer when worn and together define the waist opening 250.

As seen in FIG. 12, in the ready-to-wear, three dimensional configuration of the diaper 220, the back side ears 235 overlap the front side ears 234 when the first fastening component 284 is engaged with the second fastening component 282. It is understood, however, that the diaper 220 may instead be configured so that the front side ears 234 overlap the back side ears 235.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

Those skilled in the art will recognize that the present disclosure may be manifested in a variety of forms other than the specific embodiments described and contemplated herein. Specifically, the various features described with respect to the various embodiments and figures should not be construed to be applicable to only those embodiments and/or figures. Rather, each described feature may be combined with any other feature in various contemplated embodiments, either with or without any of the other features described in conjunction with those features. Accordingly, departure in form and detail may be made without departing from the scope of the present disclosure as described in the appended claims.

EMBODIMENTS

Embodiment 1: A method of manufacturing an absorbent web may comprise moving a foraminous forming member in a machine direction, the foraminous forming member having a forming surface and at least one masking media disposed on the forming surface and covering portions of the forming surface and leaving portions of the forming surface uncovered, applying vacuum pressure along a portion of the foraminous member so as to draw air through the forming surface in a first direction, the at least one masking media substantially blocking the air from moving through the covered portions of the forming surface, depositing fibrous material onto the forming surface to form an fibrous web corresponding to the uncovered portions of the forming surface, and disengaging the formed fibrous web from the forming surface. The at least one masking media may be flexible such that the at least one masking media may be sucked tight to the forming surface and form direct contact with the forming surface along the portion of the forming surface where vacuum pressure is applied, thereby preventing the fibrous material from flowing between the at least one masking media and the forming surface.

Embodiment 2: The method of embodiment 1, wherein the at least one masking media may be substantially impermeable to air.

Embodiment 3: The method of any of the preceding embodiments, wherein disengaging the formed fibrous web from the forming surface may comprise expelling air through the forming surface in a second direction, the second direction being generally opposite the first direction.

Embodiment 4: The method of embodiment 3, wherein the expelled air may be expelled by an air knife and at a pressure of between about 10 psi and about 10 psi.

Embodiment 5: The method of embodiment 3, wherein the expelled air may be expelled at by an air blower comprising bullet-shaped nozzles and at pressure of between about 1 psi and about 7 psi.

Embodiment 6: The method of embodiment 3, wherein the at least one masking media may be flexible such that expelling air through the forming surface in the second direction causes the masking media to flex away from the forming surface to form a gap between the at least one masking media and the forming surface.

Embodiment 7: The method of embodiment 6, wherein the gap is at least 0.25 mm.

Embodiment 8: The method of embodiment 6, wherein the gap is at least 1.0 mm.

Embodiment 9: The method of any of the preceding embodiments, wherein the at least one masking media may have a thickness of between about 0.1 mm and about 5.0 mm.

Embodiment 10: The method of any of the preceding embodiments, wherein the at least one masking media may have a thickness of between about 0.1 mm and about 2.5 mm.

Embodiment 11: The method of any of the preceding embodiments, wherein the at least one masking media may comprise a single, belt-like member.

Embodiment 12: The method of any of the preceding embodiments, wherein the at least one masking media is disposed on the forming surface such that a first end of the at least one masking media and a second end of the at least one masking media abut each other, and wherein the at least one masking media further comprises a connecting portion covering the first end of the at least one masking media and the second end of the at least one masking media.

Embodiment 13: The method of any of the preceding embodiments, wherein the at least one masking media may cover portions of the forming surface to produce a series of interconnected uncovered portions of the forming surface.

Embodiment 14: The method of embodiment 13, wherein depositing fibrous material onto the forming surface to form a fibrous web corresponding to the uncovered portions of the forming surface comprises forming a continuous fibrous web.

Embodiment 15: The method of any of the preceding embodiments, wherein the at least one masking media may cover portions of the forming surface to produce a series of individual, discrete uncovered portions of the forming surface.

Embodiment 16: The method of embodiment 15, wherein depositing fibrous material onto the forming surface to form a fibrous web corresponding to the uncovered portions of the forming surface comprises forming individual, discrete fibrous webs.

Embodiment 17: The method of any of the preceding embodiments, wherein the foraminous member further has a metal masking plate overlaying the at least one masking media.

Embodiment 18: An apparatus for forming fibrous web structures, the apparatus comprising a foraminous forming member having a forming surface and comprising a vacuum zone and a blow-off zone, wherein air is drawn through the forming surface in a first direction in the vacuum zone, at least one masking media disposed on the forming surface, the at least one masking media covering portions of the forming surface and leaving portions of the forming surface uncovered, and a fiber deposition apparatus disposed about the foraminous member and configured to introduce fibrous material proximate the foraminous member vacuum zone. The at least one masking media may be flexible such that the at least one masking media is sucked tight to the forming surface and forms direct contact with the forming surface along the portion of the foraminous member vacuum zone, thereby preventing the introduced fibrous material from flowing between the at least one masking media and the forming surface.

Embodiment 19: The apparatus of embodiment 18, wherein air may be expelled through the forming surface in a second direction in the blow-off zone, the second direction being generally opposite the first direction.

Embodiment 20: The apparatus of embodiment 19, wherein the expelled air may be expelled by an air knife and at a pressure of between about 10 psi and about 10 psi.

Embodiment 21: The apparatus of embodiment 19, wherein the expelled air may be expelled by an air blower comprising bullet-shaped nozzles and at a pressure of between about 1 psi and about 7 psi.

Embodiment 22: The apparatus of any of embodiments 19-21, wherein the at least one masking media may be flexible such that the air expelled through the forming surface in the second direction causes the at least one masking media to flex away from the forming surface to form a gap between the at least one masking media and the forming surface.

Embodiment 23: The apparatus of embodiment 22, wherein the gap is at least 0.25 mm.

Embodiment 24: The apparatus of embodiment 22, wherein the gap is at least 1.0 mm.

Embodiment 25: The apparatus of any of the preceding embodiments, wherein there may be no air forced air movement through the forming surface in the blow-off zone.

Embodiment 26: The apparatus of any of the preceding embodiments, wherein the masking media may have a first region comprising a first thickness and a second region comprising a second thickness, wherein the first thickness is less than the second thickness.

Embodiment 27: The apparatus of any of the preceding embodiments, wherein the masking media may cover portions of the forming surface to produce a series of individual, discrete uncovered portions of the forming surface, and wherein each individual, discrete uncovered portion comprises opposing lateral side portions and opposing end portions.

Embodiment 28: The apparatus of embodiment 27, wherein the masking media may have a first region comprising a first thickness and a second region comprising a second thickness, wherein the first thickness is less than the second thickness, and wherein the second region is disposed directly adjacent a first end portion of one of the individual, discrete uncovered portions of the forming surface.

Embodiment 29: The apparatus of any of the preceding embodiments, wherein the at least one masking media has a thickness of between about 0.5 mm and about 5 mm.

Embodiment 30: The apparatus of any of the preceding embodiments, wherein the at least one masking media has a thickness of between about 0.1 mm and about 2.5 mm.

Embodiment 31: The apparatus of any of the preceding embodiments, wherein the at least one masking media comprises a single, belt-like member.

Embodiment 32: The apparatus of any of the preceding embodiments, further comprising a metal masking plate disposed over the at least one masking media such that the masking media is sandwiched between the forming surface and the metal masking plate.

What is claimed is:

1. A method of manufacturing a fibrous web, the method comprising:

moving a foraminous forming member in a machine direction, the foraminous forming member having a forming surface and at least one masking media disposed on the forming surface and covering portions of the forming surface and leaving portions of the forming surface uncovered, side portions of the at least one masking media covering a portion of the foraminous forming member and inboard side edges of the at least one masking media defining at least one open area corresponding to uncovered portions of the forming surface;

applying vacuum pressure along a portion of the foraminous forming member so as to draw air through the forming surface in a first direction, the at least one masking media substantially blocking the air from moving through the covered portions of the forming surface;

depositing fibrous material onto the forming surface to form a fibrous web corresponding to the uncovered portions of the forming surface; and disengaging the formed fibrous web from the forming surface, wherein the at least one masking media is flexible such that the at least one masking media is sucked tight to the forming surface and forms direct contact with the forming surface along the portion of the forming surface where vacuum pressure is applied, thereby preventing the fibrous material from flowing between the at least one masking media and the forming surface.

2. The method of claim 1, wherein disengaging the formed fibrous web from the forming surface comprises expelling air through the forming surface in a second direction, the second direction being generally opposite the first direction.

3. The method of claim 2, wherein the expelled air is expelled by an air knife and at a pressure of between about 10 psi and about 40 psi.

4. The method of claim 2, wherein the expelled air is expelled by an air blower comprising bullet-shaped nozzles and at a pressure of between about 1 psi and about 7 psi.

5. The method of claim 2, wherein the at least one masking media is flexible such that expelling air through the forming surface in the second direction causes the masking media to flex away from the forming surface to form a gap between the at least one masking media and the forming surface.

6. The method of claim 5, wherein the gap is at least 0.25 mm.

7. The method of claim 1, wherein the at least one masking media has a thickness of between about 0.1 mm and about 5.0 mm.

8. The method of claim 1, wherein the at least one masking media comprises a single, flexible belt member.

9. The method of claim 1, wherein the at least one masking media is disposed on the forming surface such that a first end of the at least one masking media and a second end of the at least one masking media abut each other, and wherein the at least one masking media further comprises a connecting portion covering the first end of the at least one masking media and the second end of the at least one masking media.

10. The method of claim 1, wherein the at least one masking media covers portions of the forming surface to produce a series of interconnected uncovered portions of the forming surface.

11. The method of claim 1, wherein the at least one masking media covers portions of the forming surface to produce a series of individual, discrete uncovered portions of the forming surface, inboard side edges of the at least one masking media defining discrete open areas corresponding to the discrete uncovered portions.

12. An apparatus for forming fibrous web structures, the apparatus comprising:

a foraminous forming member having a forming surface and comprising a vacuum zone and a blow-off zone, wherein air is drawn through the forming surface in a first direction in the vacuum zone;

at least one masking media disposed on the forming surface, the at least one masking media covering portions of the forming surface and leaving portions of the forming surface uncovered, side portions of the at least one masking media covering side edges of the foraminous forming member and inboard side edges of the at least one masking media defining at least one open area corresponding to uncovered portions of the forming surface; and a fiber deposition apparatus disposed about the foraminous forming member and configured to introduce fibrous material proximate the vacuum zone of the foraminous forming member, wherein the at least one masking media is flexible such that the at least one masking media is sucked tight to the forming surface and forms direct contact with the forming surface along the portion of the vacuum zone of the foraminous forming member, thereby preventing the introduced fibrous material from flowing between the at least one masking media and the forming surface.

13. The apparatus of claim 12, wherein air is expelled through the forming surface in a second direction in the blow-off zone, the second direction being generally opposite the first direction.

14. The apparatus of claim 13, wherein the at least one masking media is flexible such that the air expelled through the forming surface in the second direction causes the at least one masking media to flex away from the forming surface to form a gap between the at least one masking media and the forming surface.

15. The apparatus of claim 14, wherein the gap is at least 0.25 mm.

16. The apparatus of claim 12, wherein there is no forced air movement through the forming surface in the blow-off zone.

17. The apparatus of claim 12, wherein the masking media has a first region comprising a first thickness and a second region comprising a second thickness, wherein the first thickness is less than the second thickness.

18. The apparatus of claim 12, wherein the masking media covers portions of the forming surface to produce a series of individual, discrete uncovered portions of the forming surface with inboard side edges of the masking media defining discrete open areas corresponding to the uncovered portions, and wherein each individual, discrete uncovered portion comprises opposing lateral side portions and opposing end portions.

19. The apparatus of claim 18, wherein the masking media has a first region comprising a first thickness and a second region comprising a second thickness, wherein the first thickness is less than the second thickness, and wherein the second region is disposed directly adjacent a first end portion of one of the discrete open areas.

20. The apparatus of claim 12, further comprising a metal masking plate disposed over the at least one masking media such that the masking media is sandwiched between the forming surface and the metal masking plate.

* * * * *